(12) United States Patent
Wainwright et al.

(10) Patent No.: US 7,329,538 B2
(45) Date of Patent: Feb. 12, 2008

(54) METHODS AND COMPOSITIONS FOR THE DETECTION OF MICROBIAL CONTAMINANTS

(75) Inventors: Norman R. Wainwright, Falmouth, MA (US); Foster T. Jordan, Chapin, SC (US); Frank C. Rumore, Lebanon, NJ (US); Charles Balas, Jr., Madison, CT (US)

(73) Assignee: Charles River Laboratories, Inc., Wilmington, MA (US)

( * ) Notice: Subject to any disclaimer, the term of this patent is extended or adjusted under 35 U.S.C. 154(b) by 354 days.

(21) Appl. No.: 10/803,177

(22) Filed: Mar. 17, 2004

(65) Prior Publication Data

US 2004/0241788 A1 Dec. 2, 2004

Related U.S. Application Data

(60) Provisional application No. 60/455,632, filed on Mar. 17, 2003.

(51) Int. Cl.
*C12M 1/34* (2006.01)
*C12M 3/00* (2006.01)
*C12Q 1/37* (2006.01)

(52) U.S. Cl. .................. 435/288.7; 435/23; 435/288.3; 435/288.4; 435/287.9

(58) Field of Classification Search ............. 435/288.7, 435/288.3, 288.4, 23, 287.9
See application file for complete search history.

(56) References Cited

U.S. PATENT DOCUMENTS 3,915,805 A 10/1975 Levin
3,944,391 A 3/1976 Harris et al.
3,954,663 A 5/1976 Yamamoto et al.
4,038,029 A 7/1977 Teller et al.
4,038,147 A 7/1977 Reno (Continued)

FOREIGN PATENT DOCUMENTS

EP 0121868 A1 * 10/1984

(Continued)

OTHER PUBLICATIONS

Patent Cooperation Treaty (PCT) International Search Report; International Application No. PCT/US2004/008013, mailed on Apr. 8, 2005 (9 pages including Notification of Transmittal of International Search Report).

(Continued)

*Primary Examiner*—Gladys J P Corcoran
*Assistant Examiner*—Nathan Bowers
(74) *Attorney, Agent, or Firm*—Goodwin Procter LLP

(57) ABSTRACT

The invention provides methods and compositions for the detection and/or quantification of a microbial contaminant, for example, a bacterial endotoxin or a glucan, in a sample. In particular, the invention provides a test cartridge useful in the practice of hemocyte lysate-based assays for the detection and/or quantification of a microbial contaminant in a sample. In addition, the invention provides methods of making and using such cartridges. In addition, the invention provides a rapid, sensitive, multi-step kinetic hemocyte lysate-based assay for the detection and/or quantification of a microbial contaminant in a sample. In addition, the invention provides a glucan-specific lysate that can be used in a variety of assay formats, including, for example, a test cartridge, optionally configured to perform a kinetic assay.

20 Claims, 20 Drawing Sheets

U.S. PATENT DOCUMENTS

| | | | |
|---|---|---|---|
| 4,221,865 A | 9/1980 | Dubczak et al. | |
| 4,221,866 A | 9/1980 | Cotter | |
| 4,245,044 A | 1/1981 | Kuo et al. | |
| D258,144 S | 2/1981 | Kallet et al. | |
| 4,273,557 A | 6/1981 | Juranas | |
| 4,279,774 A | 7/1981 | Lindsay et al. | |
| 4,301,245 A | 11/1981 | Lindsay et al. | |
| 4,322,217 A | 3/1982 | Dikeman | |
| 4,370,413 A | 1/1983 | Neeman et al. | |
| 4,376,819 A | 3/1983 | Brown et al. | |
| D278,182 S | 3/1985 | Aihara et al. | |
| 4,606,824 A | 8/1986 | Chu et al. | |
| 4,717,658 A | 1/1988 | Michaels | |
| 4,806,316 A | 2/1989 | Johnson et al. | |
| D325,090 S | 3/1992 | Karp et al. | |
| D330,428 S | 10/1992 | Lewis et al. | |
| 5,155,032 A | 10/1992 | Tanaka et al. | |
| 5,179,006 A | 1/1993 | Matuura et al. | |
| 5,266,461 A | 11/1993 | Tanaka | |
| D342,793 S | 12/1993 | Balmer | |
| D343,905 S | 2/1994 | Nagata et al. | |
| 5,286,625 A | 2/1994 | Tanaka et al. | |
| 5,310,657 A | 5/1994 | Berzofsky | |
| 5,316,911 A | 5/1994 | Baek et al. | |
| 5,318,893 A * | 6/1994 | Matuura et al. | 435/23 |
| D353,676 S | 12/1994 | Kelln et al. | |
| 5,372,946 A | 12/1994 | Cusak et al. | |
| 5,389,547 A | 2/1995 | Tanaka et al. | |
| 5,401,647 A | 3/1995 | Tanaka et al. | |
| 5,474,984 A | 12/1995 | Tanaka et al. | |
| 5,504,011 A | 4/1996 | Gavin et al. | |
| 5,518,006 A | 5/1996 | Mawhirt et al. | |
| 5,534,226 A | 7/1996 | Gavin et al. | |
| 5,550,030 A | 8/1996 | Tanaka et al. | |
| 5,574,023 A | 11/1996 | Shibata et al. | |
| 5,591,403 A | 1/1997 | Gavin et al. | |
| 5,591,628 A | 1/1997 | Bæk et al. | |
| 5,605,806 A | 2/1997 | Tanaka et al. | |
| 5,637,474 A | 6/1997 | Tanaka et al. | |
| D380,555 S | 7/1997 | Kurosaki et al. | |
| 5,681,710 A | 10/1997 | Tanaka et al. | |
| 5,695,948 A | 12/1997 | Tanaka et al. | |
| 5,702,882 A | 12/1997 | Tamura et al. | |
| D390,661 S | 2/1998 | Foggia | |
| D391,373 S | 2/1998 | Shartle | |
| 5,731,212 A | 3/1998 | Gavin et al. | |
| 5,750,500 A * | 5/1998 | Tsuchiya et al. | 514/11 |
| 5,795,962 A | 8/1998 | Iwanaga et al. | |
| 5,800,781 A | 9/1998 | Gavin et al. | |
| 5,836,360 A | 11/1998 | Gavin et al. | |
| 6,046,021 A | 4/2000 | Bochner | |
| D437,419 S | 2/2001 | Kraack et al. | |
| D445,909 S | 7/2001 | Pogorzelski | |
| 6,270,982 B1 | 8/2001 | Jordan et al. | |
| 6,303,389 B1 | 10/2001 | Levin et al. | |
| 6,306,659 B1 * | 10/2001 | Parce et al. | 436/47 |
| 6,391,570 B1 | 5/2002 | Jordan et al. | |
| 6,428,971 B1 | 8/2002 | Shinabarger et al. | |
| 6,440,722 B1 | 8/2002 | Knapp et al. | |
| D463,570 S | 9/2002 | Bedingham et al. | |
| 6,451,610 B1 | 9/2002 | Gorman et al. | |
| D472,324 S | 3/2003 | Rumore et al. | |
| 6,696,261 B2 | 2/2004 | Patel et al. | |
| 2003/0104501 A1 | 6/2003 | Jordan et al. | |
| 2006/0183181 A1 | 8/2006 | Wainwright et al. | |
| 2006/0216780 A1 | 9/2006 | Wainwright et al. | |

FOREIGN PATENT DOCUMENTS

| | | |
|---|---|---|
| EP | 0816513 A1 | 1/1998 |
| GB | A-2080524 | 2/1982 |
| JP | 61093958 | 5/1986 |
| WO | WO-83/02123 | 6/1983 |
| WO | WO-99/19355 | 4/1999 |
| WO | 99/53322 | 10/1999 |
| WO | WO-2005/010207 | 2/2005 |
| WO | WO-2006/076617 A2 | 7/2006 |
| WO | WO-2006/076617 A3 | 7/2006 |
| WO | WO-2007/078268 A2 | 7/2007 |

OTHER PUBLICATIONS

Patent Cooperation Treaty (PCT) Written Opinion of the International Searching Authority for PCT Application No. PCT/US2004/008013, mailed on Apr. 8, 2005 (8 pages).

Aono et al., "Interaction Between Hemocytes and Plasma Is Necessary for Hemolymph Coagulation in the Spiny Lobster, *Panulirus japonicus*," *Comp. Biochem. Physiol.* vol. 113A, No. 3, pp. 301-305 (1996).

Asokan et al., "Activation of Prophenoloxidase in the Plasma and Haemocytes of the Marine Mussel *Perna viridis* Linnaeus," *Developmental and Comparative Immunology*, vol. 21, No. 1, pp. 1-12 (1997).

Aspan et al., "cDNA cloning of prophenoloxidase from the freshwater crayfish *Pacifastacus leniusculus* and its activation," *Proc. Natl. Acad. Sci. USA*, vol. 92, pp. 939-943 (Feb. 1995).

Aspan et al., "The Effect of Endogenous Proteinase Inhibitors on the Prophenoloxidase Activating Enzyme, A Serine Proteinase from Crayfish Haemocytes," *Insect Biochem*, vol. 20, No. 5, pp. 485-492 (1990).

Bettencourt et al., "Hemolymph-Dependent and -Independent Responses in *Drosophila* Immune Tissue," *Journal of Cellular Biochemistry*, 92:849-863 (2004).

Bullis, "Invertebrate Pathology: Responses to Injury and Disease," Aquavet II, Comparative Pathology of Aquatic Animals, Laboratory for Marine Animal Health, School of Veterinary Medicine, University of Pennsylvania, undated.

Burmester et al., "Origin and evolution of anthropod hemocyanins and related proteins," *J Comp Physiol* B 172: 95-107 (2002).

Charles River Laboratories, "In Vitro Pyrogen Test (IPT)," (2002).

Charles River Laboratories, IPT Assay Steps, (2002).

"Comparative Immunology," *Department of Comparative Physiology—Uppsala University*, http://www.jamfys.ebec.uu.se/propo.html, printed May 22, 2002.

Cooper et al., "The Impact of Non-endotoxin LAL-Reactive Materials on *Limulus* Amebocyte Lysate Analyses," *PDA Journal of Pharmaceutical Science & Technology*, vol. 51. No. 1:2-6 (Jan.-Feb. 1997).

Datta et al., "Purification of a unique glycoprotein that enhances phenol oxidase activity in scorpion (*Heterometrus bengalensis*) haemolymph," *Biochem. J.* vol. 260, 525-529 (1989).

Decker et al., "SDS-induced Phenoloxidase Activity of Hemocyanins from *Limulus polyphemus, Eurypelma californicum*, and *Cancer magister*," *The Journal of Biological Chemistry*, vol. 276, No. 21, pp. 17796-17799 (May 2001).

Decker et al., "Tarantula Hemocyanin Shows Phenoloxidase Activity," *The Journal of Biological Chemistry*, vol. 279, No. 40, pp. 25889-25892 (Oct. 1998).

De Kimpe et al., "The cell wall components peptidoglycan and lipoteichoic acid from *Staphylococcus aureus* act in synergy to cause shock and multiple organ failure," *Medical Sciences*, pp. 10359-10363 (Oct. 1995).

Duner, Kristina I., "A new kinetic single-stage *Limulus amoebocyte* lysate method for the detection of endotoxin in water and plasma," *Journal of Biochemical and Biophysical Methods*, vol. 26, pp. 131-142 (1993).

Gollas-Galvan et al., "Prophenoloxidase from brown shrimp (*penaeus californiensis*) hemocytes," *Comparative Biochemistry and Physiology Part B*, 122: 77-82 (1999).

Ganguly et al., "Tyrosine Phosphorylation of a 94-kDa Protein of Human Fibroblasts Stimulated by Streptococcal Lipoteichoic Acid," *The Journal of Biological Chemistry*, vol. 260, No. 24, pp. 13342-13346 (Oct. 1985).

Geng et al., "Hemostasis in Larvae of *Manduca sexta*: Formation of A Fibrous Coagulum by Hemolymph Proteins," *Biochemical and Biophysical Research Communications*, vol. 155, No. 2, pp. 1060-1065 (Sep. 15, 1998).

Ginsburg, "Role of lipoteichoic acid in infection and inflammation", The Lancet Infectious Diseases, vol. 2, pp. 171-179 (Mar. 2002).

Goldsworthy et al., "Adipokinetic hormone enhances laminarin and bacterial lipopolysaccharide-induced activation of the prophenoloxidase cascade in the African migratory locust," *Locusta migratoria, Journal of Insect Physiology*, 48: 601-608 (2002).

Halwani et al., "Apolipophorin-III and the Interactions of Lipoteichoic Acids with the Immediate Immune Responses of *Galleria mellonella,*" *Journal of Invertebrate Pathology*, 76, 233-241 (2000).

Hamada et al., "Chemical Properties and Immunobiological Activities of Streptococcal Lipoteichoic Acids," *Abl. Bakt. Hyg.* A 259, 228-243 (1985).

Harrington et al., "Synthesis of Peptidoglycan and Teichoic Acid in *Bacillus subtilis*: Role of the Electrochemical Proton Gradient," *Journal of Bacteriology*, vol. 159, No. 3, pp. 925-933 (Sep. 1984).

Hauton et al., "Circatidal rhythmicity in the activity of the phenoloxidase enzyme in the common shore crab," *Carcinus maenas, Comp. Biochem. Physiol.* vol. 111B, No. 3, pp. 347-352 (1995).

Hauton et al., "In Situ Variability in Phenoloxidase Activity in the Shore Crab, *Carcinus maenas* (L.)," *Comp. Biochem. Physiol.* vol. 117B, No. 2, pp. 267-271 (1991).

Hernandez-Lopez et al, "In the spiny lobster (*Panulirus interruptus*) the prophenoloxidase is located in plasma not in haemocytes," *Fish & Shellfish Immunology*, 14, 105-114 (2003).

Hurley, James C., "Endotoxeima: Methods of Detection and Clinical Correlates," *Clinical Microbiology Reviews*, vol. 8, No. 2, pp. 261-292 (Apr. 1995).

Iwanaga et al., "Chromogenic Substrates for Horseshoe Crab Clotting Enzyme: Its Application for the Assay of Bacterial Endotoxins," *Hemostasis*, Chapter 7, pp. 183-188 (1978).

Iwanaga, Sadaaki, "The limulus clotting reaction," *Current Opinion in Immunology. Current Biology Ltd.*, vol. 5, No. 5, pp. 74-82 (1993).

Iwanaga, "The molecular basis of innate immunity in the horseshoe crab," *Curr Opin Immunol*, vol. 14, pp. 87-95 (2002).

Jiang et al., "Characterization and Functional Analysis of 12 Naturally Occuring Reactive Site Variants of Serpin-1 from *Manduca sexta* -," *The American Society for Biochemistry and Molecular Biology, Inc.*, vol. 272, No. 2, pp. 1082-1087 (Jan. 1997).

Jiang et al., "Pro-phenol oxidase activating proteinase from an insect, *Manduca sexta*: A bacteria-inducible protein similar to *Drosophila* easter," *Biochemistry*, vol. 95, Issue 21, 12220-12225 (Aug. 1998).

Jiang et al., "β-1, 3-Glucan recognition protein-2 (βGRP-2) from *Manduca sexta*: an acute-phase protein that binds β-1, 3-Glucan and lipoteichoic acid to aggregate fungi and bacteria and stimulate prophenoloxidase activation," *Insect Biochemistry and Molecular Biology*, vol. 34, Issue 1, pp. 89-100 (2004).

Johansson et al., "Cellular Immunity in Crustaceans and the proPO System," *Parasitology Today.*, vol. 5, No. 6 (1989).

Jolliffe et al., "The Energized Membrane and Cellular Autolysis in *Bacillus subtilis*," *Cell*, vol. 25, pp. 753-763 (Sep. 1981).

Kawabata et al., "The Clotting Cascade and Defense Molecules Found in the Hemolymph of the Horseshoe Crab," *New Directions in Invertebrate Immunology*, 255-283 (1996).

Kobayashi et al., "Detection of peptidoglycan in human plasma using the silkworm larvae plasma test," *FEMS Immunology and Medical Microbiology*, 28: 49-53 (2000).

Lackie et al., "Invertebrate immunity," *Parasitology*, 80: 393-412 (1980).

Loker et al., "On Being A Parasite in an Invertebrate Host: A Short Survival Course," *J. Parasitol.*, 80(5), p. 728-747 (1994).

Mattsson et al., "Highly Purified Lipoteichoic Acid from *Staphylococcus aureus* Induces Procoagulant Activity and Tissue Factor Expression in Human Monocytes but Is a Weak Inducer in Whole Blood: Comparison with Peptidoglycan," *Infection and Immunity*, pp. 4322-4326 (Jul. 2004).

Morath et al., "Structural Decomposition and Heterogeneity of Commercial Lipoteichoic Acid Preparatiions," *Infection and Immunity*, pp. 938-944 (Feb. 2002).

Muta et al., "Limuls Factor C," *Journal of Biological Chemistry, American Society of Biological Chemists*—Baltimore, MD, vol. 266. No. 10 pp. 6554-6561 (1991).

Nagai et al., "A Link between Blood Coagulation and Prophenol Oxidase Activation in Arthropod Host Defense," *The Journal of Biological Chemistry*, vol. 275, No. 38, pp. 29264-29267 (Sep. 2000).

Nagai et al., "Functional Conversion of Hemocyanin of Hemocyanin to Phenoloxidase by Horseshoe Crab Antimicrobial Peptides," *The Journal of Biological Chemistry*, vol. 26, No. 29, pp. 27166-27170 (Jul. 2001).

Nellaiappan et al., "On the Presence of Prophenoloxidase in the Hemolymph of the Horseshoe Crab," *Limulus, Comp. Biochem. Physiol.*, vol. 113B, No. 1, pp. 163-168 (1996).

Obayashi et al., "A new chromogenic endotoxin-specific assay using recombined limulus coagulation enzymes and its clinical applications," *Clin. Chin. Acta* 149:55-65 (1985).

Parrinello et al., "Phenoloxidases in ascidian hemocytes: characterization of the pro-phenoloxidase activating system," *Comparative Biochemistry and Physiology Part B: Biochemistry and Molecular Biology*, vol. 135, Issue 4, pp. 583-591 (2003).

Pearson et al., "Comparison of Chemical Analyses of Hollow-Fiber Dialyzer Extracts," *Artificial Organs*, vol. 8, No. 3:291-298 (1984).

Ratcliffe et al., "Activation of the Prophenoloxidase Cascade and Initiation of Nodule Formation in Locusts by Bacterial Lipopolysaccharides," *Developmental and Comparative Immunology*, vol. 15, pp. 33-39 (1991).

Roslansky et al., "Sensitivity of *Limulus* Amebocyte Lysate (LAL) to LAL-Reactive Glucans," *Journal of Clinical Microbiology*, vol. 29, No. 11:2477-2483 (Nov. 1991).

Saul et al., The Majority of Prophenoloxidase in the Hemolymph of *Manduca sexta* is Present in the Plasma and Not in the Hemocytes, *Developmental and Comparative Immunology*, Vo. 11, pp. 479-485 (1987).

Seki et al., "Horseshoe Crab (1,3)-β-D-Glucan-sensitive Coagulation Factor G," *The Journal of Biological Chemistry*, vol. 269, No. 2:1370-1374 (Jan. 1994).

Shah et al, "A novel glucan-binding protein with lipase activity from the oral pathogen *Streptococcus mutans,*" *Microbiology*, 150: 1947-1956 (2004).

Söderhäll, "Prophenoloxidase Activating System and Melanization—A Recognition Mechanism of Arthropods? A Review.," *Developmental and Comparative Immunology*, vol. 6, pp. 601-611 (1982).

Söderhäll et al., "The Prophenoloxidase Activating System and its Role in Invertebrate Defence," *Annuals of the New York Academy of Sciences*, vol. 712, pp. 155-161 (Apr. 15, 1994).

Söderhäll et al., "Chapter 15 The Prophenoloxidase Activating System: The Biochemistry of Its Activation and Role in Arthropod Cellular Immunity, with Special Reference to Crustaceans," *Immunity in Invertebrates*, pp. 208-223 (1986).

Sritunyalucksana et al., "Peroxinectin, a cell adhesive protein associated with the proPO system from the black tiger shrimp," *Penaeus monodon, Developmental and Comparative Immunology*, 25: 353-363 (2001).

Sugumaran et al., "Lysolecithin—A Potent Activator of Prophenoloxidase from the Hemolymph of the Lobster," *Homarus Americanas, Biochemical and Biophysical Research Communications*, vol. 176, No. 3, pp. 1371-1376 (1991).

Tarsi-Tsuk et al., Stimulation of the Respiratory Burst in Peripheral Blood Monocytes by Lipoteichoic Acid, *The Journal of Immunology*, vol. 144, No. 7, pp. 2665-2670 (Apr. 1990).

"The Horseshoe Crab", http://www.horseshoecrab.org/anat/amat.html, printed Aug. 6, 2002.

"The prophenoloxidase (proPO) activation system", http://sbs.umkc.edu/yux/PPO%20activation.html, printed Apr. 16, 2003.

Tsuchiya et al., "Detection of peptidoglycan and β-glucan with silkworm larvae plasma test,"*FEMS Immunology and Medical Microbiology*, 15: 129-134 (1996).

Tsuji et al., "Automation of Chromogenic Substrate *Limulus* Amebocyte Lysate Assay Method for Endotoxin by Robotic System," *Applied and Environmental Microbiology*, vol. 45, No. 3, pp. 550-555 (Sep. 1984).

Vargas-Albores et al., "An Anticoagulant Solution for Haemolymph Collection and Prophenoloxidase Studies of Penaeid Shrimp (*Penaeus californiensis*)," *Comp. Biochem. Physiol*, vol. 106A, No. 2, pp. 299-303 (1993).

Wilson et al., "Identity of limulus amoebocyte lysate-active root surface materials from periodontally involved teeth," *Jounral of Clinical Periodontology*, vol. 13, No. 8, pp. 743-747 (Sep. 1986).

Patent Cooperation Treaty (PCT) International Search Report; International Application No. PCT/US98/20823; mailed Mar. 3, 1999.

Patent Cooperation Treaty (PCTP IPER; International Application No. PCT/US98/20823; mailed Jan. 24, 2000.

Patent Cooperation Treaty (PCT) Invitation to Pay Additional Fees and Partial International Search; International Application No. PCT/US04/08013; mailed Dec. 10, 2004.

"The proPO-system", Department of Comparative Physiology, Uppsala University, available at http://www.jamfys.ebc.se/propo.html, printed May 22, 2002.

Decker et al., "Recent findings on phenoloxidase activity and antimicrobial activity of hemocyanins," *Developmental & Comparative Immunology*, vol. 28, pp. 673-687 (2004).

Coates, D.A., "Enhancement of the Sensitivity of the Limulus Assay for the Detection of Gram Negative Bacteria," (1977) Journal of Applied Bacteriology 42: 445-449.

Inada et al., "A Silkworm Larvae Plasma Test for Detecting Peptidoglycan in Cerebrospinal Fluid is Useful for the Diagnosis of Bacterial Meningitis," (2003) Microbiology and Immunology, 47:(10): 701-707.

Janda et al., "A Colorimetric Estimation of Lipopolysaccharides," (1970) Febs Letters 16: (4): 343-354.

Maeda et al., "Chromogenic Assay Method of Lipopolysaccharide (LPS) for Evaluating Bacterial Standing Crop in Seawater," (1979) Journal of Applied Bacteriology 47: 175-182.

Sigma Chemical Company E-Toxate Technical Bulletin (2000) No. 210: 1-4.

Wiegel et al., "Determination of the Gram Type Using the Reaction Between Polymyxin B and Lipopolysaccarides of the Outer Cell Wall of Whole Bacteria," Journal of General Microbiology (1982) 28: 2261-2270.

Charles River Laboratories, "LAL Products and Services" (2001).

Prior, Richard B. Ed., (1990) "Clinical Applications of the Limulus Amebocyte Lysate Test" CRC Press, pp. 28-34.

Patent Cooperation Treaty (PCT) International Search Report ; International Application No. PCT/US2005/043426, completed Jul. 18, 2007 and mailed Aug. 9, 2007 (4 pages).

\* cited by examiner

METHODS AND COMPOSITIONS FOR THE DETECTION OF MICROBIAL CONTAMINANTS

RELATED APPLICATIONS

This application claims priority to and the benefit of U.S. Ser. No. 60/455,632, filed Mar. 17, 2003, the contents of which are incorporated by reference herein.

FIELD OF THE INVENTION

The present invention relates generally to methods and compositions for detecting and/or quantifying microbial contaminants in a sample. More particularly, the invention relates to methods and compositions using a hemocyte lysate for detecting and/or quantifying microbial contamination in a sample.

BACKGROUND OF THE INVENTION

Microbial contamination by, for example, Gram positive bacteria, Gram negative bacteria, yeast, fungi, and molds may cause severe illness and, in some cases, even death in humans. Manufacturers in certain industries, for example, the pharmaceutical, medical device, and food industries, must meet exacting standards to verify that their products do not contain levels of microbial contaminants that would otherwise compromise the health of the recipient. These industries require frequent, accurate, and sensitive testing for the presence of such microbial contaminants to meet certain standards, for example, standards imposed by the United States Food and Drug Administration (USFDA) or Environmental Protection Agency. By way of example, the USFDA requires certain manufacturers of pharmaceuticals and invasive medical devices to establish that their products are free of detectable levels of Gram negative bacterial endotoxin.

Furthermore, when people become infected with Gram negative bacteria, the bacteria may produce and secrete fever-inducing bacterial endotoxins. Bacterial endotoxins can be dangerous and even deadly to humans. Symptoms of infection may range from fever, in mild cases, to death. In order to promptly initiate proper medical treatment, it usually is important to identify, as early as possible, the presence of an endotoxin and, if possible, the concentration of the endotoxin in the patient.

To date, a variety of assays have been developed to detect the presence and/or amount of a microbial contaminant in a test sample. One family of assays use hemocyte lysates prepared from the hemolymph of crustaceans, for example, horseshoe crabs. These assays typically exploit, in one way or another, a clotting cascade that occurs when the hemocyte lysate is exposed to a microbial contaminant. A currently preferred hemocyte lysate is amebocyte lysate (AL) produced from the hemolymph of a horseshoe crab, for example, *Limulus polyphemus, Tachypleus gigas, Tachypleus tridentatus*, and *Carcinoscorpius rotundicauda*. Amebocyte lysates produced from the hemolymph of *Limulus, Tachypleus*, and *Carcinoscorpius* species are referred to as *Limulus* amebocyte lysate (LAL), *Tachypleus* amebocyte lysate (TAL), and *Carcinoscorpius* amebocyte lysate (CAL), respectively.

Routine assays that use LAL include, for example, gel clot assays, end point turbidometric assays, kinetic turbidometric assays, and endpoint chromogenic assays (Prior (1990) "Clinical Applications of the *Limulus* Amebocyte Lysate Test" CRC PRESS 28-34). These assays, however, suffer from one or more disadvantages including reagent expense, assay speed and limited sensitivity ranges. Also, these assays typically require that samples be sent to a testing facility removed from the origin of the sample being tested. As a result, it may take hours to weeks before a problem can be detected and remedied. Accordingly, there is an ongoing need for faster and more sensitive methods, and portable test systems employing such methods, that overcome the need to submit samples to an off-site testing facility.

SUMMARY OF THE INVENTION

The invention is based, in part, upon the discovery that it is possible to make and use optical cartridges containing an immobilized hemocyte lysate for use in hemocyte lysate-based assays. These cartridges may be used alone or in combination with optical detectors, for example, hand held optical detectors, to permit the assay of samples in the field, thereby obviating the need to send samples to an off-site testing facility. Accordingly, the cartridges can be used in a point-of-use test system. In addition, the invention is based, in part, upon the discovery of a rapid, sensitive, multi-step kinetic assay for determining the presence and/or amount of microbial contaminant in a sample of interest. This type of assay can be implemented in a cartridge, or in any other desirable assay format. In addition, the invention is based, in part, upon the discovery of a glucan-specific hemocyte lysate and a method of making such a lysate. The glucan-specific lysate may be incorporated into such a cartridge and/or used in a multi-step kinetic assay.

In one aspect, the invention provides a test cartridge for determining the presence and/or amount of a microbial contaminant in a sample. The cartridge comprises a housing defining at least one fluid inlet port, at least one optical cell, and at least one conduit having a fluid contacting surface that connects and thus provides fluid flow communication between the fluid inlet port and the optical cell. The cartridge further comprises a hemocyte lysate disposed on a first region of the fluid contacting surface of the conduit, so that when a sample is applied to the fluid inlet port, the sample traverses the region and solubilizes the hemocyte lysate during transport of the sample-lysate mixture to the optical cell. This type of cartridge can be used to perform, for example, endpoint turbidometric and kinetic turbidometric assays.

The cartridge optionally may further comprise a chromogenic substrate that acts as a substrate for one or more of the enzymes in the hemocyte lysate. The chromogenic substrate may be disposed in the first region, for example, combined with the hemocyte lysate. In this format, the sample resolubilizes or starts to resolubilize the hemocyte lysate and chromogenic substrate at substantially the same time. This type of cartridge can be used to perform, for example, a kinetic chromogenic assay. Alternatively, the chromogenic substrate may be disposed on a second region of the fluid contacting surface of the conduit, so that when the sample moves along the conduit toward the optical cell it contacts and reconstitutes the hemocyte lysate and chromogenic substrate at different regions of the conduit. In one embodiment, the second region is located downstream of the first region (i.e., the second region is located closer to the optical cell than the first region). This type of cartridge can be used to perform, for example, endpoint chromogenic and multi-step kinetic chromogenic assays, as discussed in more detail herein below.

In addition, a pre-selected amount of an agent representative of a microbial contaminant, or "spike", such as a bacterial endotoxin, a (1→3)-B-D glucan, or other microbial cell wall constituent, is disposed on a region of the fluid contacting surface of the conduit. The inclusion of the agent or spike is particularly useful as it provides a positive control to demonstrate that an assay is working, and can also demonstrate whether an inhibitor or enhancer is present in the sample. The agent or spike may be disposed on the first region, the second region, or on another region of the conduit.

It is contemplated that the number of fluid inlet ports, optical cells, and conduits in a particular cartridge may vary depending on the number of samples or microbial contaminants being tested at a particular time. A cartridge may be used to simultaneously assay duplicates of the same sample or simultaneously assay two or more different samples of interest. Alternatively, two or more different hemocyte lysates may be disposed on the cartridge so that it is possible to determine the presence and/or amount of two or more different microbial contaminants at substantially the same time. In addition, several chromogenic substrates with different enzyme specificities and optical properties, for example, light absorption transmission, and/or fluorescent properties, may be applied to the cartridge. This may permit the detection of two or more different microbial contaminants at substantially the same time.

In one embodiment, the cartridge comprises a housing that defines (i) a first fluid inlet port, a first optical cell, and a first conduit having a fluid contacting surface that connects and thus provides fluid flow communication between the first fluid inlet port and the first optical cell, and (ii) a second fluid inlet port, a second optical cell, and a second conduit having a fluid contacting surface that connects and thus provides fluid flow communication between the second fluid inlet port and the second optical cell. Within the housing, a first hemocyte lysate is disposed on a first region of the fluid contacting surface of the first conduit, so that when a sample is applied to the first fluid inlet port, the sample traverses the region and reconstitutes and/or solubilizes the first hemocyte lysate during transport to the first optical cell. Also within the housing, a second hemocyte lysate is disposed on a first region of the fluid contacting surface of the second conduit, so that when a sample is applied to the second fluid inlet port, the sample traverses the region and reconstitutes and/or solubilizes the second hemocyte lysate during transport to the second optical cell.

In one embodiment, a chromogenic substrate is disposed on a second region of the fluid contacting surface of the first conduit and/or a chromogenic substrate is disposed on a second region of the fluid contacting surface of the second conduit. In each embodiment, the second region preferably is located downstream of the first region in each conduit. In another embodiment, different chromogenic substrates may be disposed on fluid contacting surfaces of the first and second conduits so that two different reactions may be monitored in the same cartridge.

In another embodiment, a pre-selected amount of an agent representative of a microbial contaminant or spike is disposed on the fluid contacting surface of the first or second conduit. The spike may be disposed on the first region or on another region of the conduit. The spike may be useful as a positive control for the assay (i.e., indicates whether a valid test was run), and may also provide information on whether an enhancer or inhibitor is present in the sample.

As will be discussed in more detail below, the cartridges of the invention may be adapted for use in a variety of different assays. The presence of a microbial contaminant may be indicative of, for example, past or present bacterial, yeast, fungal, or mold infection. It is contemplated that, by using the appropriate hemocyte lysate, the cartridge may be used to detect the presence of a bacterial, yeast, fungal, or mold contaminant in a sample. The cartridges of the invention are particularly useful at detecting the presence, and/or determining the amount, of a Gram negative bacterial endotoxin or glucan in a sample.

During use, a sample to be tested is introduced into the sample inlet port of the cartridge and is allowed to move to the optical cell. Movement of the sample along the conduit can be passive or can be induced by an external force, for example, via positive or negative pressure in the conduit. For example, the sample can be pulled along the conduit to the optical cell via suction induced by a pump connected to a pump port located downstream of the optical cell. A change in an optical property of the sample is detected in the optical cell, the change being indicative of the presence of a microbial contaminant in the sample. In addition, the time in which a pre-selected change occurs in an optical property of the sample can be determined and compared against a predetermined standard curve to determine the concentration of the microbial contaminant in the sample. The optical property may include a color change, a change in absorbance or transmittance, a change in turbidity, a change in fluorescence or other change that can be detected in a detector, spectrophotometer or the like. The change in the optical property may be, for example, an increase in absorbance of light of a pre-selected wavelength, or may be a decrease in transmission of light of a pre-selected wavelength. As discussed below, the cartridge may be adapted to perform any one of a number of endpoint or kinetic chromogenic, or turbidometric assays.

In another aspect, the invention provides methods of preparing the cartridge by disposing, for example, by drying, a hemocyte lysate onto a solid surface of at least one conduit of the cartridge. The hemocyte lysate may then be reconstituted into an active form upon resolubilization of the hemocyte lysate. A volume of a mixture comprising a hemocyte lysate of interest and a resolubilizing agent and/or an anti-flaking agent is applied to the surface of at least one conduit and dried. The hemocyte lysate used will depend upon the assay for which the cartridge will be used. The resolubilizing agent is an agent that, either alone or in combination with another resolubilizing agent, facilitates the resolubilization of one or more components of the hemocyte lysate once the lysate is exposed to a fluid sample. The resolubilizing agent preferably also stabilizes the lysate in its dried form. The resolubilizing agent provided in the mixture facilitates the stability of the reagents and their dissolution during the assay. Resolubilizing agents include, for example, one or more sugars, salts, or combinations thereof. Preferred sugar resolubilizing agents include, for example, mannitol, mannose, sorbitol, trehalose, maltose, dextrose, sucrose, and other monosaccharides or disaccharides. The anti-flaking agent included in the mixture further stabilizes the reagents and reduces flaking of the dried lysate. The anti-flaking agent preferably also stabilizes the lysate in its dried form. Preferred anti-flaking agents include, for example, one or more polymers, for example, polyethylene glycol, polyvinyl pyrolidone, polyvinyl alcohol, mannitol, dextran, and proteins, for example, serum albumin.

In one embodiment, the lysate/resolubilizing agent/anti-flaking agent mixture is disposed in a first region of at least one conduit of the cartridge. The mixture then is dried onto a surface of the conduit in an environment having a temperature of about 4° C. to about 40° C., more preferably, from about 10° C. to about 35° C., more preferably, from about 15° C. to about 30° C. and a relative humidity of about 0% to about 30%, more preferably, from about 2% to about 20%, more preferably, from about 4% to about 10%. Preferably, the temperature is about 25° C. and the relative humidity is about 5%. Drying preferably occurs for about 10 minutes to about 8 hours, more preferably for about 1 hour in a temperature regulated drying chamber. The lysate/resolubilizing agent/anti-flaking agent mixture optionally may also include an agent representative of a microbial contamination (i.e., a spike), for example, a bacterial endotoxin, a (1→3)-B-D glucan or other microbial cell wall constituents.

In another embodiment, the mixture is dried onto the surface of the conduit by lyophilization or freeze drying, for example, at temperatures below 0° C., for example, from about −75° C. to about −10° C., more preferably from about −30° C. to about −20° C.

In addition, a chromogenic substrate, comprising a resolubilizing agent and an anti-flaking agent is applied to a second region of the cartridge and dried onto the cartridge as described above. The chromogenic substrate may comprise an anti-frothing agent, for example, polyvinyl alcohol and polypropylene glycol.

Although the drying procedure is discussed in relation to a test cartridge, the drying procedure can be used to dry the lysate onto a variety of different solid supports. For example, the method can also be used to dry the lysate on the surface of a well disposed within or defined by a solid support, for example, a 12-well or a 96-well plate.

In another aspect, the invention provides an improved method referred to as a two-step or multi-step kinetic assay for detecting the presence and/or quantifying the amount of a particular microbial contaminant in a sample. The sample to be tested is contacted with a hemocyte lysate comprising an activatable enzyme, for example, a pro-clotting enzyme or a clotting enzyme, that is activated if the microbial contaminant is present in the sample. After contacting the sample with the lysate, the sample-lysate mixture is incubated for a preselected period of time. Then, the sample-lysate mixture is contacted with a substrate, for example, a chromogenic substrate, for the activated enzyme. If the sample-lysate substrate mixture contains an activated enzyme, the activated enzyme produces a change in the substrate, which in turn produces a predetermined change in an optical property of the sample-lysate-substrate mixture. The time in which the predetermined change occurs then is determined. The resulting time then is compared to a predetermined standard curve to determine whether the microbial contaminant is present in the sample and/or to determine the amount of microbial contaminant present in the sample. For example, the concentration of microbial contaminant in a sample can be measured by comparing the time required to produce the predetermined change in the optical property against a predetermined standard curve of the microbial contaminant. Using this type of assay, it is possible to adjust the timing of the steps to produce an assay of predetermined sensitivity and duration.

The optical property measured can be a change (e.g., an increase or decrease) in an optical property, for example, absorbance at a particular wavelength, transmittance at a particular wavelength, fluorescence at a particular wavelength, or optical density. For example, the optical property may be a change in absorbance or transmittance at a wavelength in the range from about 200 nm to about 700 nm, and more preferably in the range from about 350 nm to about 450 nm.

The chromogenic substrate may be any substrate for a lysate enzyme that is activated (e.g., hydrolyzed) to cause a detectable chromogenic or fluorogenic change, for example, by release of a chromophore or a fluorophore, that is detectable by an optical detector. In one embodiment, the chromogenic substrate for LAL contains a para-nitroaniline chromophore, such as that, for example, in the chromogenic substrate acetate-Ile-Glu-Ala-Arg-pNA. The proteases in the LAL cleave colorless tetrapeptide to release the pNA group, which causes a color change. Cleavage of the tetrapeptide simulates the cleavage reaction of the proteases in the LAL with coagulogen, a clotting component that contains the tetrapeptide. As a result, by using this chromophore, it is possible to measure the progress of the reaction by measuring the change in optical density at about 395 nm. Other chromophores may include dinitrophenyl alanine, cyclohexyl alanine and the like. Alternatively, the substrate may contain a fluorophore, for example, 7-amino-4-methyl coumarin, 7-amino-4-trifluoromethyl coumarin, and 4-methoxy-2-naphthalyamine. Fluorogenic substrates for LAL that contain N-methylcoumarin as a leaving group are available from Enzyme Systems Products, Livermore, Calif.

The multi-step kinetic assay may be performed in a variety of formats, for example, in a tube, cuvette, cartridge, well on a solid support (such as a 96-well multi-well plate), or other vessel suitable for use in combination with an optical detector, for example, a spectrophotometer, fluorimeter, luminometer, or the like.

In another aspect, the invention provides a method for producing an amebocyte lysate depleted of Factor C activity. The method comprises the steps of: (a) providing a preparation of amebocytes; and (b) lysing the amebocytes in the presence of at least 0.05M salt to provide an amebocyte lysate preparation depleted of Factor C activity. The method optionally includes the step of, after step (b), removing cellular debris, for example, cell membranes, and then harvesting the remaining lysate. The cellular debris may be sedimented by centrifugation and the remaining supernatant harvested.

In one embodiment, the salt may comprise a monovalent cation, for example, a sodium or potassium salt. Salts useful in the practice of the invention include, for example, sodium chloride, potassium chloride, sodium acetate, and potassium acetate. The salt concentration can be in the range from 0.15 M to about 6 M, more preferably from about 0.25 M to about 4 M, and more preferably from about 1 M to 2 M. However, the precise concentration of salt necessary to remove or reduce Factor C activity may be determined by routine experimentation. For example, amebocytes can be lysed in the presence of difference concentrations of salt, and the residual lysates can then be checked to see whether a coagulin clot forms in the presence of a bacterial endotoxin. The foregoing method can produce a glucan-specific amebocyte lysate that is substantially free of Factor C activity. The lysate, therefore, retains Factor G activity but is depleted of Factor C activity.

In another aspect, the invention provides an amebocyte lysate substantially free of Factor C activity, wherein the lysate comprises at least about 0.25M salt and wherein the lysate is capable of producing a coagulin gel in the presence of glucan. The lysate may comprise, from about 0.25 M salt to about 6 M salt, from about 0.5 M salt to 4 M salt, and from about 1 M to about 2 M salt. In one embodiment, the salt contains a monovalent cation, for example, a sodium ion or a potassium ion. For example, the salt may include sodium chloride, potassium chloride, sodium acetate, potassium acetate, or a combination thereof.

The foregoing and other objects, features and advantages of the present invention will be made more apparent from the following drawings and detailed description of preferred embodiments of the invention.

BRIEF DESCRIPTION OF THE DRAWINGS

The objects and features of the invention may be better understood by reference to the drawings described below in which.

FIGS. 5A-5D are schematic illustrations of an exemplary cartridge in which FIG. 5A is a view of a bottom half of an exemplary cartridge of the invention showing the locations of immobilized hemocyte lysate and chromogenic substrate, FIG. 5B is a view of a top half of an exemplary cartridge of the invention showing the location of an immobilized agent representative of a microbial contaminant (i.e., spike), FIG. 5C is a cross-sectional view of the fabricated cartridge through section A-A', and FIG. 5D is a cross-sectional view of the fabricated cartridge through section B-B';

FIG. 6A-6D are schematic illustrations of two exemplary cartridges, in which FIG. 6A is a top view of a first embodiment of a cartridge, FIG. 6B is a side view of the first embodiment of the cartridge pictured in FIG. 6A, FIG. 6C is a top view of a second, different embodiment of a cartridge, and FIG. 6D is a side view of the second embodiment of the cartridge of FIG. 6C;

FIG. 8A-8B are schematic illustrations showing a cartridge in combination with an exemplary optical detector in which FIG. 8A shows the cartridge being inserted into the detector, and FIG. 8B shows the cartridge actually inserted into the detector;

FIG. 10A shows the absorbance values of endotoxin standards (1.0 Endotoxin Units (EU)/mL (A1), 0.5 EU/mL (A2), 0.25 EU/mL (A3), and 0.125 EU/mL (A4)) over time in an endpoint chromogenic assay performed in a cartridge of the invention, and FIG. 10B shows a standard curve generated by plotting the absorbance values of each concentration of endotoxin at T=780 seconds;

FIG. 11A shows the absorbance values of a 5.0 EU/mL endotoxin standard, FIG. 11B shows the absorbance values of a 0.5 EU/mL endotoxin standard, FIG. 11C shows the absorbance values of a 0.05 EU/mL endotoxin standard, and FIG. 11D is a standard curve generated by plotting the log of endotoxin concentration (X-axis) versus the log of absorbance value at onset time (Y axis);

FIG. 16A represents assays performed using lipopolysaccharide, and FIG. 16B represents assays performed using glucan. Row A in each Figure represents standard LAL containing both the Factor C and Faction G cascades, Row B in each Figure represents glucan-specific lysate (i.e., Factor G-specific lysate) prepared by lysing amebocytes in 1M sodium chloride and Row C represents glucan-specific lysate prepared by lysing amebocytes in 2M NaCl. Columns 1-5 represent several dilutions of the lipopolysaccharide (10 ng/ml, 1 ng/ml, 100 pg/ml, 10 pg/ml, 0) or glucan (100 µg/ml, 10 µg/ml, 1 µg/ml, 100 ng/ml, 0) added to each sample, wherein the concentration decreases from column 1 to column 5;

In the drawings, which are not necessarily drawn to scale, like characters refer to the same or similar parts throughout the Figures.

DETAILED DESCRIPTION OF THE INVENTION

Figure 1:
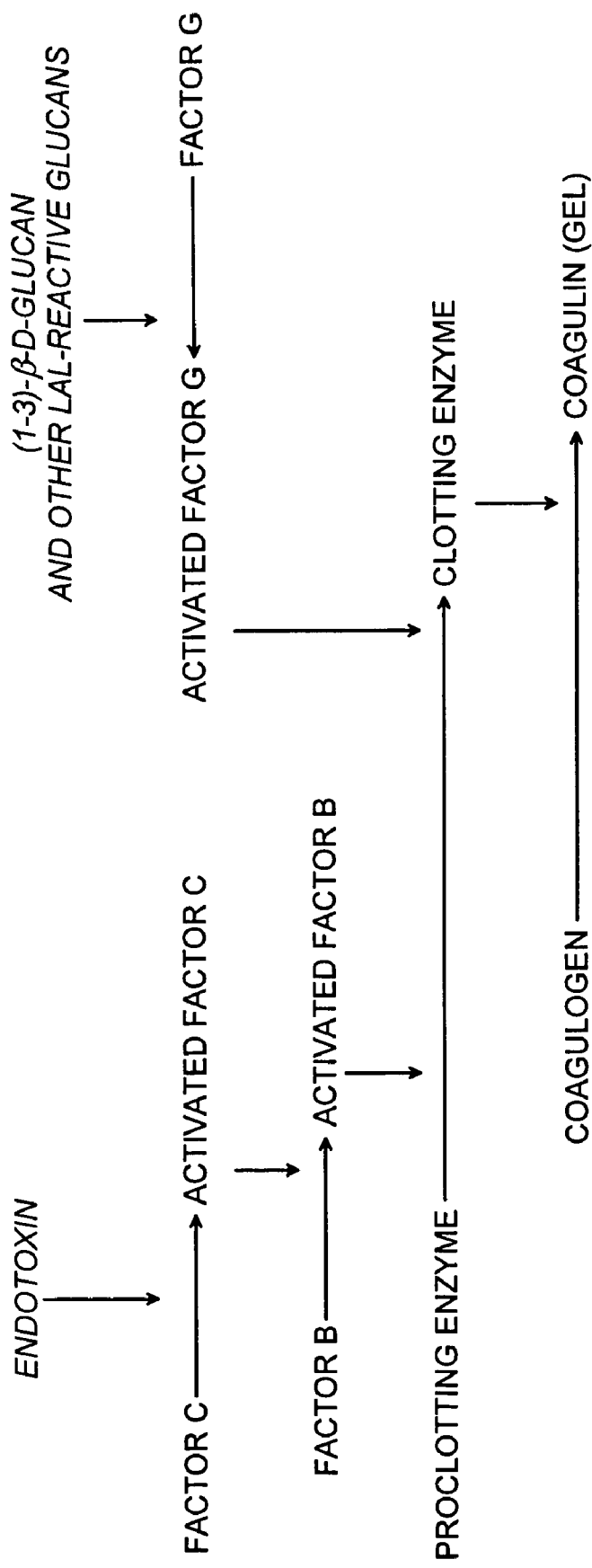
FIG. 1 is a schematic representation of the coagulation system present in amebocytes.

The invention provides an optical cartridge containing an immobilized hemocyte lysate for use in hemocyte-lysate based assays. These cartridges may be used alone or together with an optical detector, for example, a hand held optical detector. In addition, the invention provides a rapid, sensitive, broad range, multi-step assay that is useful in determining the presence and/or amount of a microbial contaminant in a sample. Although the cartridge and method may be used separately, they are particularly effective when combined together to provide a system that can be used in the field to provide rapid test results. This facilitates quicker elimination and/or treatment of microbial contamination. In addition, the invention provides a Factor C specific lysate for detecting the presence and/or amount of glucan in a sample. The lysate, therefore, can be used to determine the presence and/or amount of a yeast or mold contaminant in a sample.

The Cartridge

It is contemplated that the cartridges of the invention may be formulated with one or more hemocyte lysates and used in a variety of assays to detect the presence and/or amount of a microbial contaminant in a sample. A number of hemocyte lysate-based assays for the detection and/or quantification of a microbial contaminant can be performed in the cartridge of the invention, for example, as illustrated in FIG. 2. The cartridge may be used on its own and the test result detected by eye or may be used in combination with an optical detector, for example, a hand-held optical detector as shown and described in U.S. Pat. No. Des. 390,661.

By way of example and as illustrated in FIGS. 2A-2D, cartridge 1 has a substantially planar housing fabricated, for example, from a moldable biocompatible material. The housing may be fabricated from any material, however, transparent and/or translucent glass or polymers are preferred. Preferred polymers include, for example, polystyrene, polycarbonate, acrylic, polyester, optical grade polymers, or any plastic such that the optical cell is substantially transparent. The housing contains at least one fluid inlet port 4, at least one optical cell 6, and at least one conduit 8 having a fluid contacting surface for providing fluid flow communication between the fluid inlet port 4 and optical cell 6. The only requirements for the optical cell 6 are that it defines a void capable of containing a sample to be tested and that a portion of the optical cell 6 is transparent to light. Cartridge 1 may also have at least one pump port 12 in fluid flow communication with fluid inlet port 4 and optical cell 6 for attaching the cartridge 1 to a pump. The pump may then impart a negative pressure via pump port 12 to pull the sample from fluid inlet port 4 to optical cell 6. A hemocyte lysate is disposed on a first region 14 of the fluid contacting surface of conduit 8, so that when a sample is applied to fluid inlet port 4, the sample traverses region 14 and solubilizes or reconstitutes the hemocyte lysate into the sample as it moves toward optical cell 6. This type of cartridge 1 may be used for performing, for example, an endpoint turbidometric or a kinetic turbidometric assay. In an embodiment, a chromogenic substrate may also optionally be applied to the surface of the conduit 8 at first region 14 together with the hemocyte lysate. This type of cartridge 1 may be used for performing, for example, a kinetic chromogenic assay.

In a preferred embodiment, as illustrated in FIGS. 2A-2D, a second region 16 of the fluid contacting surface of conduit 8 is spaced apart from and downstream of first region 14. In this configuration, hemocyte lysate is disposed at first region 14 and a chromogenic substrate is disposed at second region 16, so that after the sample is contacted with the hemocyte lysate in region 14, the sample-lysate mixture traverses conduit 8 and contacts the chromogenic substrate in region 16. The sample-lysate-substrate mixture then traverses conduit 8 to optical cell 6. This type of cartridge may be used for performing, for example, an endpoint chromogenic assay or a multi-step kinetic chromogenic assay, as discussed in more detail below.

Depending upon the type of assay to be performed, a pre-selected amount of an agent representative of a microbial contaminant, or "spike," such as a bacterial endotoxin, is disposed on first region 14 of the fluid contacting surface of one or more conduits 8. Alternatively, the spike may be disposed on a different region of the conduit 8.

Figure 3A:
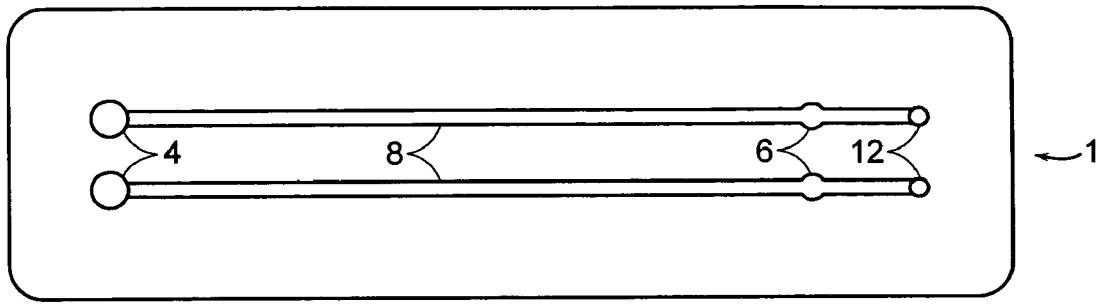
FIG. 3A-3B are schematic illustrations of an exemplary cartridge of the invention wherein each conduit has a separate fluid inlet port (FIG. 3A), and wherein two conduits share a single common fluid inlet port (FIG. 3B)
Figure 3B:
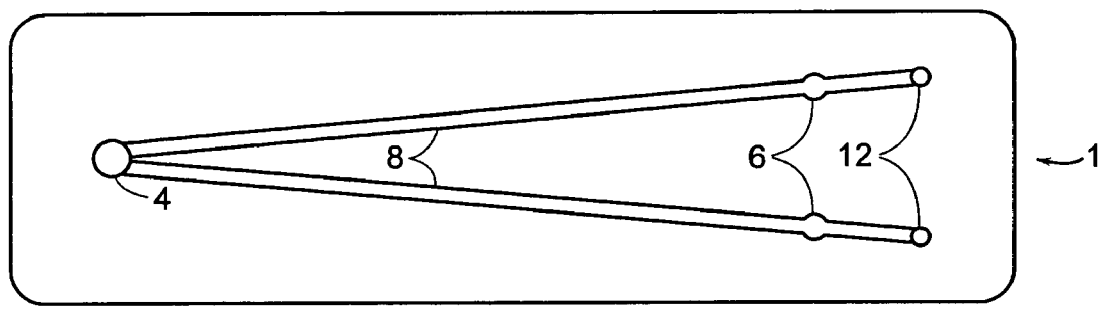
Figure 4A:
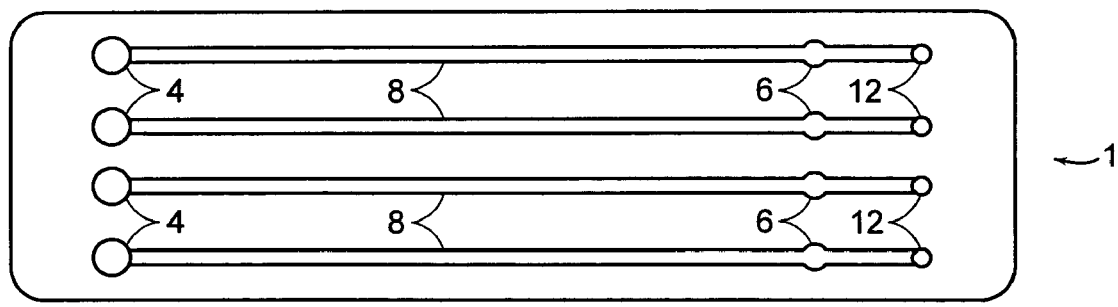
FIGS. 4A-4B are schematic illustrations of an exemplary cartridge of the invention wherein each conduit has its own fluid inlet port (FIG. 4A), and wherein a pair of conduits share a single common fluid inlet port (FIG. 4B)
Figure 4B:
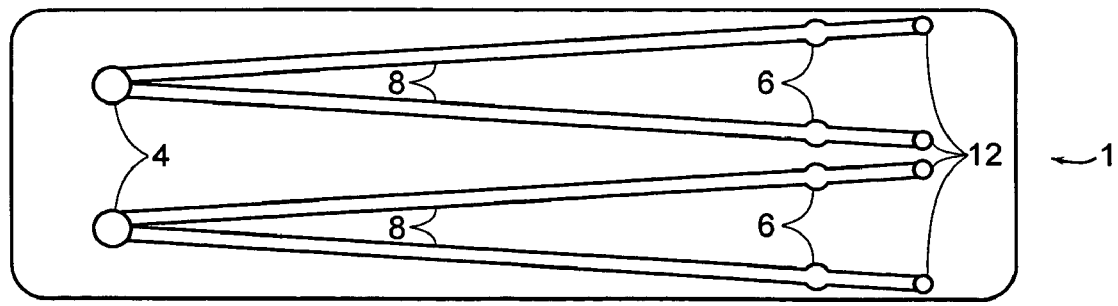

It is contemplated that the cartridge 1 may have a variety of different configurations, demonstrated, for example, in FIGS. 3 and 4. FIG. 3A shows a cartridge 1 comprising two conduits 8 with each conduit 8 having its own sample inlet port 4. FIG. 3B shows a cartridge 1 comprising two conduits 8 with each conduit 8 sharing a common sample inlet port 4. FIG. 4A shows a cartridge 1 comprising four separate conduits 8 with each conduit 8 having its own sample inlet port 4. FIG. 4B shows a cartridge 1 comprising two pairs of conduits 8, with each pair having its own sample inlet port 4.

The cartridges can be designed and used according to the type and/or number of tests required. For example, a single sample may be tested, for example, in duplicate or triplicate, for example, for research laboratory uses or for medical device and biopharmaceutical testing. Alternatively, two or more different samples may be tested individually, for example, for dialysis facility testing of water and dialysate. The cartridge preferably is a single-use, disposable cartridge that is discarded after one use. The cartridge of the invention can use approximately 20-100 fold less hemocyte lysate per sample than is used in the conventional endpoint chromogenic or kinetic chromogenic assays performed in multi-well plates, and thus provides a less costly and environmentally-friendlier test.

Once a particular assay format has been chosen, the cartridge may be fabricated as discussed below.

Cartridge Fabrication

All the reagents and materials used to prepare the cartridge preferably are free of the microbial contaminant for which the cartridge ultimately will be used to test.

It is contemplated that the cartridge may be fabricated with any hemocyte lysate of interest. As used herein, the term, "hemocyte lysate" is understood to mean any lysate or a fraction or component thereof, produced by the lysis and/or membrane permeabilization of hemocytes, for example, amebocytes and hemolymph cells, (i) extracted from a crustacean or insect and/or (ii) cultured in vitro after extraction from the host. Hemocyte cellular material that has been extruded from hemolymph cells by contact with a membrane permeabilization agent such as a $Ca^{2+}$ ionophore or the like (i.e., extruded other than by lysis) or otherwise extracted without cellular lysis is also considered to be a hemocyte lysate. A preferred hemocyte lysate is an amebocyte lysate prepared from the blood of a crustacean, for example, a horseshoe crab or Jonah crab. It is also contemplated that hemocyte lysate may include a cocktail of one or more natural (e.g., purified) or synthetic components of the enzyme cascades shown in FIG. 1.

As used herein, the term "amebocyte lysate" is understood to mean any lysate or fraction or component thereof produced by the lysis, extrusion, or extraction of the cellular contents from amebocytes extracted from a crustacean, for example, a horseshoe crab. The amebocyte lysate comprises at least one component of an enzymatic cascade (for example, as shown in FIG. 1) and/or produces a clot in the presence of an endotoxin, for example, a Gram negative bacterial endotoxin and/or a glucan, for example, a (1→3)-β-D glucan, produced by a yeast or a mold. Preferred amebocyte lysates can be derived from horseshoe crabs, which include crabs belonging to the *Limulus* genus, for example, *Limulus polyphemus*, the *Tachypleus* genus, for example, *Tachypleus gigas*, and *Tachypleus tridentatus*, and the *Carcinoscorpius* genus, for example, *Carcinoscorpius rotundicauda*.

Crude lysates may be produced using the procedure as originally described in Levin et al. (1968) Thromb. Diath. Haemorrh. 19: 186, with modification, or in Prior (1990) "Clinical Applications of the *Limulus* Amebocyte Lysate Test" CRC Press 28-36 and 159-166, and in U.S. Pat. No. 4,322,217. Other lysates may include those, for example, described in U.S. Pat. Nos. 6,270,982 and 6,391,570.

Presently, LAL is employed as the amebocyte lysate of choice in many bacterial endotoxin assays because of its sensitivity, specificity, and relative ease for avoiding interference by other components that may be present in a sample. LAL, when combined with a sample containing bacterial endotoxin and optionally with certain LAL substrates, reacts with the endotoxin in the sample to produce a detectable product, such as a gel, increase in turbidity, or a colored or light-emitting product, in the case of a synthetic chromogenic substrate. The product may be detected, for example, either visually or by the use of an optical detector.

As shown in FIG. 1, the coagulation system of hemolymph, like the mammalian blood coagulation system, comprises at least two coagulation cascades that include an endotoxin-mediated pathway (the Factor C pathway) and a (1→3)-B-D glucan-mediated pathway (the Factor G pathway). See, for example, Morita et al. (1981) FEBS Lett. 129: 318-321 and Iwanaga et al. (1986) J. Protein Chem. 5: 255-268.

The endotoxin-mediated activation of LAL is well understood and has been thoroughly documented in the art. See, for example, Levin et al. (1968) supra; Nakamura et al. (1986) Eur. J. Biochem. 154: 511; Muta et al. (1987) J. Biochem. 101: 1321; and Ho et al. (1993) Biochem. & Mol. Biol. INT. 29: 687. When bacterial endotoxin is contacted with LAL, the endotoxin initiates a series of enzymatic reactions, referred to in the art as the Factor C pathway, that can involve three serine protease zymogens called Factor C, Factor B, and pro-clotting enzyme (see, FIG. 1). Briefly, upon exposure to endotoxin, the endotoxin-sensitive factor, Factor C, is activated. Activated Factor C thereafter hydrolyses and activates Factor B, whereupon activated Factor B activates proclotting enzyme to produce clotting enzyme. The clotting enzyme thereafter hydrolyzes specific sites, for example, $Arg^{18}$-$Thr^{19}$ and $Arg^{46}$-$Gly^{47}$ of coagulogen, an invertebrate, fibrinogen-like clottable protein, to produce a coagulin gel. See, for example, U.S. Pat. No. 5,605,806.

It is possible to produce an endotoxin-specific lysate by removing Factor G activity from the lysate, such as the Factor G depleted lysates produced by the methods described in U.S. Pat. Nos. 6,391,570 and 6,270,982. Also, it is contemplated that lysates may be depleted of Factor G activity by the addition of certain inhibitors or modulators of Factor G activity, for example, certain detergents, saccharides, polysaccharides, and other reagents described in U.S. Pat. Nos. 5,155,032; 5,179,006; 5,318,893; 5,474,984; 5,641,643; 6,270,982; and 6,341,570. An endotoxin-specific lysate is a lysate capable of reacting with a bacterial endotoxin but in which the reactivity to (1→3)-B-D glucan has been depleted by at least 80%, more preferably by at least 90%, and more preferably by at least 95% relative to the crude lysate from which the endotoxin-specific lysate was prepared.

(1→3)-B-D glucans and other LAL reactive glucans, produced by microorganisms such as yeasts and molds, can also activate the clotting cascade of LAL, through a different enzymatic pathway, referred to in the art as the Factor G pathway (see, FIG. 1). Factor G is a serine protease zymogen that becomes activated by (1→3)-β-D glucan or other LAL reactive glucans. Upon exposure to (1→3)-β-D glucan, for example, Factor G is activated to produce activated Factor G. Activated Factor G thereafter converts the proclotting enzyme into clotting enzyme, whereupon the clotting enzyme converts coagulogen into coagulin.

As used herein, the term, "(1→3)-β-D glucan" is understood to mean any water soluble polysaccharide, disaccharide or derivative thereof that is (i) capable of inducing formation of a coagulin clot in crude *Limulus* amebocyte lysate, and (ii) contains at least two β-D glucosides, connected by a (1→3)-β-D glycosidic linkage (see Formula I). It is contemplated that such a polysaccharide or derivative thereof, in addition to containing a (1→3)-β-D glycosidic linkage, may also contain glucoside moieties connected by a variety of other glycosidic linkages, for example, via a (1→4)-β-D glycosidic linkage and/or by a (1→6)-β-D glycosidic linkage. It is contemplated that such (1→3)-β-D glucans may be isolated from a variety of sources including, without limitation, plants, bacteria, yeast, algae, and fungi, or alternatively may be synthesized using conventional sugar chemistries.

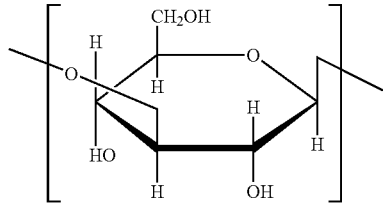

Formula I

It is possible to produce a (1→3)-B-D glucan specific lysate by producing a lysate depleted of Factor C activity. As shown herein, it is possible to produce a glucan-specific lysate by lysing amebocytes in the presence of at least 0.15 M salt, more preferably 0.25 M salt, for example, a salt containing a monovalent cation, such as sodium or potassium ions. For example, the amebocytes are lysed in about 0.15 M to about 6 M salt, for example, sodium chloride. Alternatively, the amebocytes are lysed in a solution containing from about 0.25 M to about 4 M salt, or from about 1 M to about 2M salt. When using sodium chloride, it appears that the amoeboctye preparation loses substantial Factor C activity when the amebocytes are lysed in a solution containing 0.25 M sodium chloride. However, the concentration of other salts necessary to produce a comparable results may be determined by routine titration experiments. For example, amebocytes may be lysed in different concentrations of salt and the resulting lysates examined for their ability to produce a coagulin gel in the presence of a Gram negative bacterial endotoxin. The concentration of salt may be chosen where the resulting lysate has lost a substantial amount of reactivity to the bacterial endotoxin. Other salts that may be used include, but are not limited to, monovalent ionic salts, such as, potassium chloride, potassium acetate and sodium acetate. An exemplary method for producing a glucan specific lysate is described in Example 4. A glucan-specific lysate is a lysate capable of reacting with glycan, for example, (1→3)-β-D glucan, but in which reactivity to a bacterial endotoxin or lipopolysaccharide has been depleted by at least 80%, more preferably at least 90%, and more preferably at least 95% relative to the crude lysate from which the glucan-specific lysate was prepared.

Methods for enhancing the sensitivity of hemocyte lysate for endotoxin, for example, may include, without limitation, aging the crude hemocyte lysate, adjusting pH, adjusting the concentration of divalent cations, adjusting the concentration of coagulogen, chloroform extraction, and the addition of serum albumin, biocompatible buffers and/or biological detergents.

As will be apparent to one of ordinary skill, divalent metal salts, which are known to promote activation of the pro-clotting enzyme of hemocyte lysate, as well as buffers to avoid extremes of pH that could inactivate the clotting enzyme preferably are included in the lysate. Any of the buffers and salts that are understood in the art to be compatible with the amebocyte lysate system may be used. Typical formulation additives may include, without limitation, about 100-300 mM NaCl, about 10-100 mM divalent cations (e.g., $Mg^{2+}$ or $Ca^{2+}$), biocompatible buffers, e.g., Tris (tris(hydroxy)aminomethane), to give a final pH of about 6.0 to about 8.0, and, if the lysate is to be freeze dried, then sugars, e.g., mannitol or dextran. It is contemplated that the choice of appropriate formulation additives may also be determined by routine experimentation.

Synthetic chromogenic substrates have been used to measure the level of endotoxin-activated pro-clotting enzyme in LAL prepared from the hemolymph of both *Tachypleus tridentatus* and *Limulus polyphemus* horseshoe crabs (Iwanaga et al. (1978) Hemostasis 7: 183-188). During an LAL assay that uses a chromogenic substrate, the pro-clotting enzyme (a serine protease) in the LAL is activated by endotoxin and cleaves the substrate's peptide chain on the carboxyl side of arginine so as to release the chromogenic group from the substrate, thereby releasing a marker compound that can be easily detected by, for example, spectrophotometry. One advantage of using a synthetic chromogenic substrate in an LAL assay in place of a conventional LAL gelation test is that the amount of activated clotting enzyme can be quantified and correlated to endotoxin levels in the sample.

Any chromogenic substrate that is cleaved by the clotting enzyme of a hemocyte lysate may be used in the practice of the invention. U.S. Pat. No. 5,310,657, for example, describes an exemplary chromogenic substrate having the formula $R_1$-$A_1$-$A_2$-$A_3$-A4-B-$R_2$, where $R_1$ represents hydrogen, a blocking aromatic hydrocarbon or an acyl group; $A_1$ represents an L or D-amino acid selected from Ile, Val or Leu; $A_2$ represents Glu or Asp; $A_3$ represents Ala or Cys; $A_4$ represents Arg; B represents a linkage selected from an ester and an amide; and $R_2$ represents a chromogenic of fluorogenic group which is covalently attached to the C-carboxyl terminal of Arginine through the B linkage, the fluorogenic or chromogenic moiety being capable of being cleaved from the remainder of the chromogenic substrate to produce a chromogen or a fluorogen. An exemplary chromogenic substrate has the consensus sequence acetate-Ile-Glu-Ala-Arg-pNA, where pNA represents a para-nitroaniline group. U.S. Pat. No. 4,188,264 describes a peptide substrate with a structure consisting of L-amino acids in the sequence $R_1$-Gly-Arg-$R_2$ where $R_1$ represents an N-blocked amino acid and $R_2$ is a group that can be released by enzymatic hydrolysis to yield a colored compound, $HR_2$. U.S. Pat. No. 4,510,241 discloses a chromogenic peptide substrate, which differs from the previous substrate in that the Gly moiety is replaced in the sequence by Ala or Cys. Alternatively, the chromogenic substrate may contain a fluorophore, for example, 7-amino-4-methyl coumarin, 7-amino-4-trifluoromethyl coumarin, and 4-methoxy-2-naphthalyamine.

Inhibition or enhancement of the assay occurs when substances in the test sample interfere with the hemocyte lysate reaction. Inhibition results in a longer reaction time, indicating lower levels of microbial contamination than may actually be present in the test sample. Enhancement results in shorter reaction time, indicating higher levels of microbial contamination than may actually be present in the test sample. To verify the lack of inhibition or enhancement, an aliquot of test sample (or a dilution of the test sample) is "spiked" with a known amount of an agent representative of the microbial contaminant to be measured. It is recommended that the microbial contaminant spike results in a final microbial contaminant concentration in the sample equal to the mid-point, on a log basis, between the microbial contaminant concentration of the highest and lowest standards in the standard curve. For example, in an assay with a standard curve spanning from 50 Endotoxin Units (EU)/mL to 0.005 EU/mL, samples should be spiked to contain a final microbial contaminant concentration of 0.5 EU/mL. In an assay with a standard curve spanning from 1 EU/mL to 0.01 EU/mL, the microbial contaminant spike should result in a final microbial contaminant concentration of 0.1 EU/mL.

The spiked sample is assayed in parallel with the unspiked sample. The resulting microbial contaminant concentration in the unspiked sample and the microbial contaminant recovered in the spiked sample then are calculated. The microbial contaminant recovered should equal the known concentration of the spike within about 25%. If the test sample (or dilution) is found to inhibit or enhance the reaction, the sample may require further dilution until the inhibition or enhancement is overcome. Initially, one may want to screen for inhibition or enhancement by testing 10-fold dilutions of test sample. Once the approximate non-inhibitory or non-enhancing dilution is determined, the exact dilution can be found by testing two-fold dilutions around this dilution. The degree of inhibition or enhancement will be dependent upon the concentration of the test sample. If several concentrations of the same sample are to be assayed, it is necessary to establish performance characteristics for each concentration independently.

In fabricating the cartridge of the invention, it is helpful to combine the amebocyte lysate and chromogenic substrate with at least one resolubilizing agent, such as a sugar or salt, and at least one anti-flaking agent, such as a polymer, prior to drying the lysate onto the solid support.

The resolubilizing agent preferably stabilizes the lysate in the dried form and facilitates resolubilization of the reagents during the assay. Useful resolubilizing agents include, for example, mannitol, mannose, sorbitol, trehalose, maltose, dextrose, sucrose, and other monosaccharides and disaccharides. The hemocyte lysate and chromogenic substrate preferably contain from about 0.01% (w/v) to about 20% (w/v), more preferably from about 0.1% (w/v) to about 1.0% (w/v) of the resolubilizing agent prior to drying.

The anti-flaking agent is an agent that prevents or reduces the likelihood that the hemocyte lysate and/or chromogenic substrate becomes disassociated from a solid support in the form of a dry flake. The anti-flaking agent preferably also stabilizes the hemocyte lysate or chromogenic substrate in the dried form. Useful anti-flaking agents include, for example, one or more polymers, including, for example, polyethylene glycol, polyvinyl pyrolidone, dextrans, mannitol, and proteins, for example, serum albumin. The lysate preferably contains from about 0.01% (w/v) to about 25% (w/v), more preferably from about 0.1% (w/v) to about 1.0% (w/v) of anti-flaking agent prior to drying.

In addition, it has been found that certain polymers reduce the formation of air bubbles (e.g., frothing) when the hemocyte lysate and/or chromogenic substrate are resolubilized. Useful anti-frothing agents include polyvinyl alcohol and polypropylene glycol. In order to reduce frothing, the lysate and/or chromogenic substrate may contain from about 0.01% (w/v) to about 10% (w/v), more preferably from about 0.1% (w/v) to about 1.0% (w/v) anti-frothing agent prior to drying.

Figure 5A:
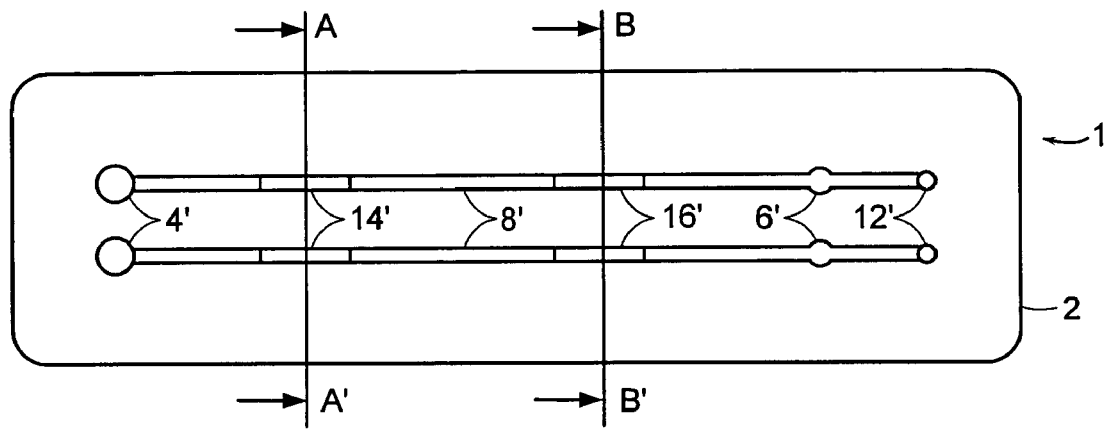
Figure 5B:
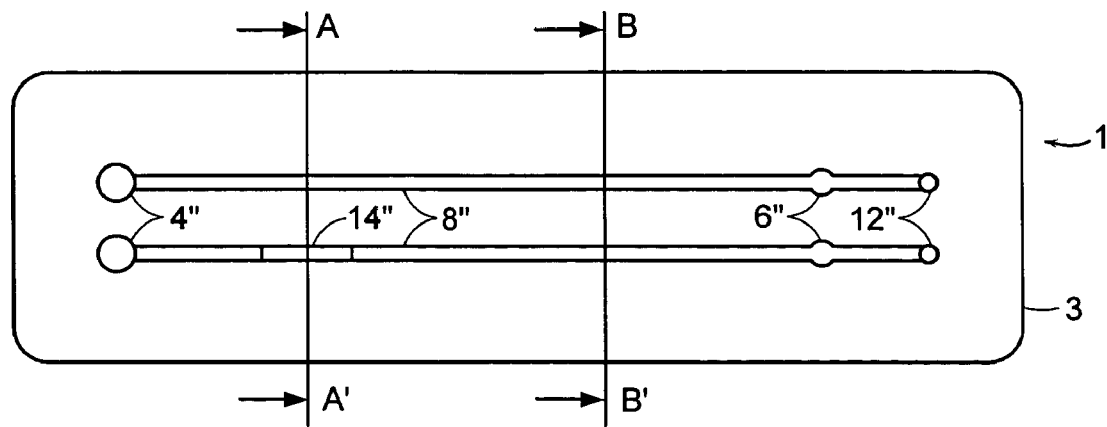

An exemplary fabrication process for the cartridge is described with reference to FIG. 5, in which FIG. 5A represents a bottom half 2 of cartridge 1 and FIG. 5B represents a top half 3 of cartridge 1. Once prepared, the two halves of the cartridge 1 are joined to one another by adhesive, solvent bonding, ultrasonic welding, snap fit joints, or the like.

In FIG. 5A, the bottom half 2 of the cartridge 1 defines one half of each conduit 8' (each having a first region 14' and a second region 16'). During fabrication of the bottom half 2 of the cartridge 1, hemocyte lysate is applied to each first region 14' and chromogenic substrate is applied to each second region 16'. In FIG. 5B, the top half 3 of the cartridge 1 defines one half of each conduit 8''. During fabrication of top half 3 of the cartridge 1, an agent representative of a microbial contaminant (i.e., a spike), for example, a preselected amount of an endotoxin, is applied to region 14''. Once the reagents have been applied to the respective top 3 and bottom 2 halves of the cartridge 1, the cartridge halves 2 and 3 then are dried under conditions that preserve the activity of the hemocyte lysate and permit reconstitution of the hemocyte lysate to produce active lysate. In order to preserve the activity of the reagents during drying, the cartridge halves 2 and 3 are placed in an environment having a temperature from about 4° C. to about 40° C., more preferably, from about 10° C. to about 35° C., more preferably, from about 15° C. to about 30° C., and a relative humidity from about 0% to about 30%, more preferably, from about 2% to about 20%, more preferably from about 4% to about 10%. Preferred drying conditions include a temperature of about 25° C. and a relative humidity of about 5%. An exemplary protocol for manufacturing a cartridge of the invention is provided in Example 1.

In an alternative approach, the hemocyte lysate may be dried via freeze drying under standard conditions, about −30° C. to about −40° C. under vacuum.

Figure 5C:
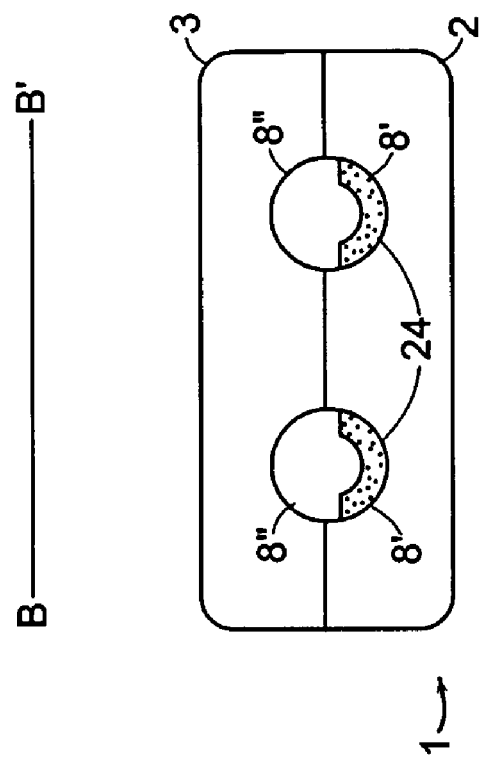
Figure 5D:
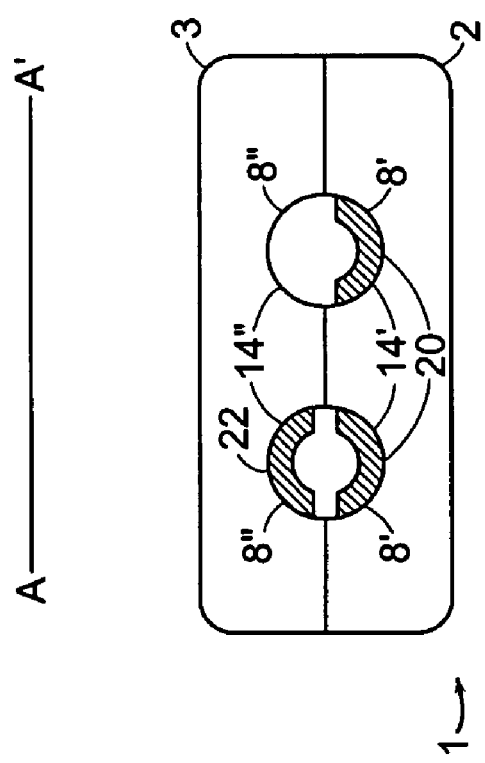

After drying, the two cartridge halves 2 and 3 are joined to one another to create an intact cartridge 1. FIG. 5C is a cross-sectional view through Section A-A' in which the two halves of the conduit (namely 8' and 8'') together create an intact conduit 8, wherein region 14' of the bottom 8' of each conduit contains immobilized hemocyte lysate 20 and region 14'' of the top 8'' of one conduit contains immobilized endotoxin 22. FIG. 5D is a cross-sectional view through Section B-B' in which region 16' of the bottom 8' of each conduit contains immobilized chromogenic substrate 24.

Figure 6A:
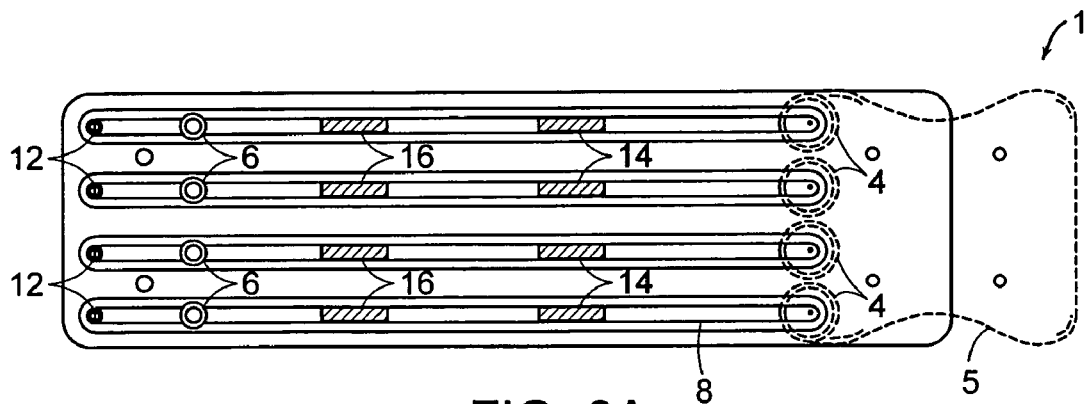
Figure 6B:
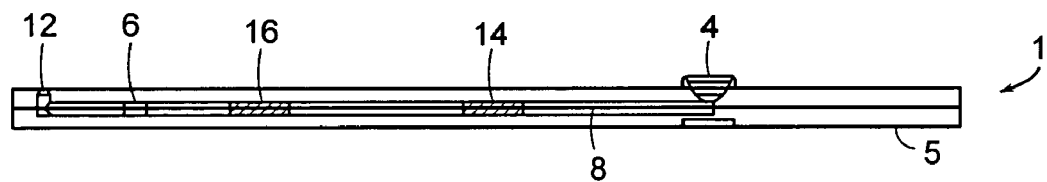
Figure 6C:
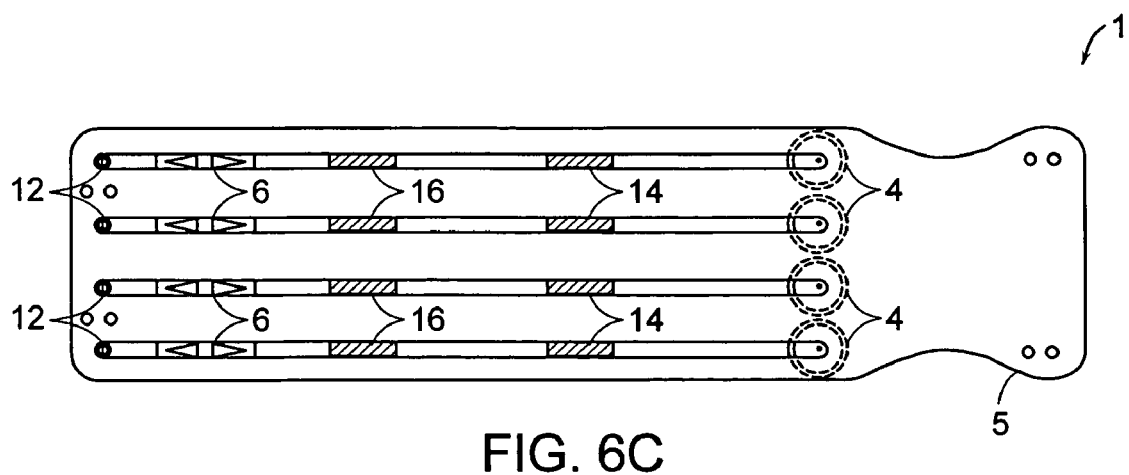
Figure 6D:
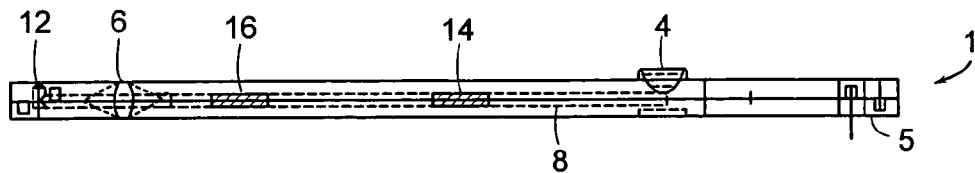

FIGS. 6A-6D are illustrations of two exemplary cartridges 1 of the invention corresponding to FIGS. 6A-6B and FIGS. 6C-6D. In FIG. 6A, the cartridge 1 may have an alternative finger grip 5 as shown with the dashed line. FIGS. 6A and 6B illustrate that the optical cell 6 in the first cartridge 1 is substantially cylindrical in shape. In FIG. 6C, the cartridge 1 also has a similar finger grip 5 to that shown by the dashed line in FIG. 6A. FIGS. 6C and 6D illustrate that the optical cell 6 in second cartridge 1 is more elongate in shape. The elongate shape permits greater depth and rise of fluid for greater optical pathlength and proportionally greater detection sensitivity. In addition, it is contemplated that the top and bottom halves 2 and 3 of each cartridge 1 may comprise one or more male (female) members and one or more reciprocal and interfitting female (male) members to stack the unassembled cartridge halves one on top of the other, as well as provide mating alignment in the assembled state.

The dimensions of a particular cartridge 1 may vary depending upon the number and/or type of assays to be performed. However, in one embodiment, as shown schematically in FIG. 6A, for example, the cartridge 1 has a length of about 10.16 cm (4.00"), width of about 2.54 cm (1.00"), and a height of about 0.476 cm (0.188"). The bore of the conduit 8 running from the fluid inlet port 4 to the optical cell 6 is about 0.127 cm (0.050"), where the lysate is dried on a region 14 of the conduit 8 about 2.381 cm (0.938") from the fluid inlet port 4, and a chromogenic substrate is dried on a region 16 of the conduit 8 about 4.65 cm (1.831") from the fluid inlet port 4. The optical cell 6 in this embodiment is dimensioned to accommodate about 25 μL of sample.

Specimen Collection and Preparation

The cartridge may be used to determine the level of microbial contamination in a fluid, for example, a fluid to be administered locally or systemically, for example, parenterally to a mammal, or a body fluid to be tested for infection, including, for example, blood, lymph, urine, serum, plasma, ascites fluid, lung aspirants, and the like. In addition, the cartridge may be used to determine the level or microbial contamination in a water supply, for example, a supply of drinking water. In addition, the cartridge may be used to determine the level of microbial contamination in a food product, pharmaceutical, or medical device.

In general, materials used to harvest, store, or otherwise contact a sample to be tested, as well as test reagents, should be free of microbial contamination, for example, should be pyrogen-free. Materials may be rendered pyrogen-free by, for example, heating at 250° C. for 30 minutes. Appropriate precautions should be taken to protect depyrogenated materials from subsequent environmental contamination.

Representative Assays that can be Performed in the Cartridge

It is contemplated that a variety of hemocyte lysate assays may be used in the cartridge of the invention, such as, for example, the end point turbidometric assay, the kinetic turbidometric assay, the endpoint chromogenic assay, and the single-step kinetic assay. In addition, the cartridge of the invention may be used with the multi-step kinetic assay, as described herein.

1. End Point Turbidometric Assay

The end point turbidometric assay is described in Prior (1990) supra, pp. 28-34. Briefly, the end point turbidimetric assay includes the steps of (i) solubilizing a hemocyte lysate with a sample to be analyzed, (ii) incubating the resulting mixture at a temperature of about 0° to about 40° C., preferably about 25° to about 40° C., for a predetermine and (iii) measuring the increase in turbidity as a result of coagulation, if any, using a conventional coagulometer, nephrometer, or spectrophotometer.

Figure 2A:
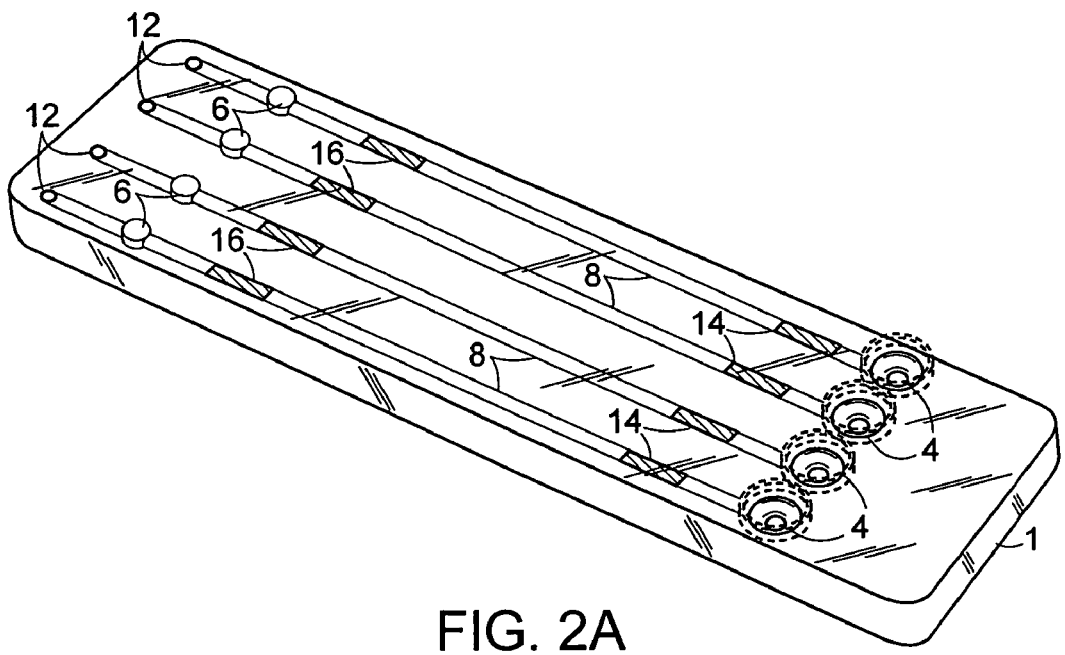
FIGS. 2A-2D are schematic illustrations of an exemplary cartridge of the invention in perspective view (FIG. 2A), top view (FIG. 2B), side view (FIG. 2C), and end view (FIG. 2D)
Figure 2B:
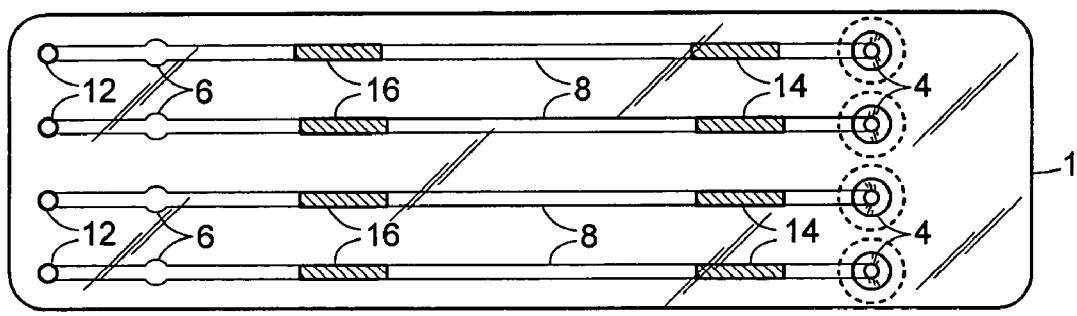
Figure 2C:
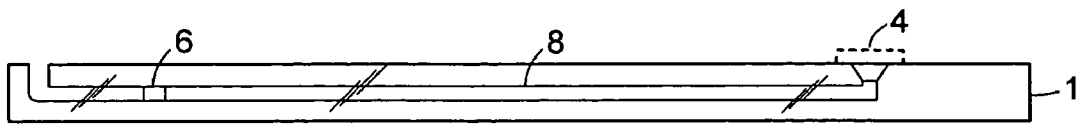
Figure 2D:
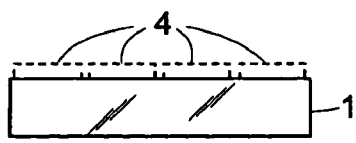

Referring to FIG. 2A, in order to perform an endpoint turbidometric assay in a cartridge 1, a sample is moved, for example, to a first region 14 of the conduit 8 containing the hemocyte lysate, where it is solubilized, for example, by cycling between forward and reverse pump action. The sample-lysate mixture then is moved to optical cell 6 for measurement of an optical property, for example, turbidity, using an optical detector. Results from multiple assays, for example, two assays can be averaged. The optical density of the sample-lysate mixture at a certain predetermined time point may then be interpolated onto a predetermined standard curve, for example, showing turbidity values on the Y axis versus endotoxin concentration on the X axis, to give the concentration of the microbial contaminant in the sample.

2. Kinetic Turbidometric Assay

The kinetic turbidometric assay is described in Prior (1990) supra, pp. 28-34. Briefly, the kinetic turbidimetric assay includes the steps of (i) solubilizing a hemocyte lysate with a sample to be analyzed, (ii) incubating the resulting mixture at a temperature of about 0° to about 40° C., preferably about 25° to about 40° C., over a predetermined time range, and (iii) measuring a time required for either a turbidity change caused by coagulation to reach a pre-selected value or a ratio in change of the turbidity, using a conventional coagulometer, nepherometer, or spectrophotometer.

Referring to FIG. 2A, in order to perform a kinetic turbidometric assay in a cartridge 1, a sample is, for example, moved to a first region 14 of the conduit 8 containing the hemocyte lysate, where it is solubilized, for example, by cycling between forward and reverse pump action. The sample-lysate mixture then is moved to optical cell 6 for measurement of an optical property, for example, turbidity, by measuring the absorbance or transmittance properties of the sample-lysate mixture using an optical detector. The detector may determine how long it takes for each optical property to exhibit, for example, a 5% drop in optical transmittance. Results from multiple assays, for example, two assays can be averaged. The resulting values may then be interpolated onto a predetermined standard curve, for example, showing time for a preselected change in transmittance on the Y axis versus endotoxin concentration on the X axis, to give the concentration of the contaminant in the sample.

3. Endpoint Chromogenic Assay

The endpoint chromogenic assay is described in Prior (1990) supra, pp. 28-34, and U.S. Pat. Nos. 4,301,245 and 4,717,658. Briefly, the endpoint chromogenic assay includes the steps of (i) solubilizing a hemocyte lysate preparation with a sample to be analyzed, (ii) incubating the resulting mixture at a temperature of about 0° C. to about 40° C., preferably about 25° C. to about 40° C., for a predetermined time, (iii) contacting a test device containing chromogenic substrate with the incubated sample-lysate mixture, (iv) adding a reaction inhibitor, and (v) measuring, e.g., by colorimetric change, a substance released from the synthetic substrate by protease activity.

Referring to FIG. 2A, in order to perform an endpoint chromogenic assay in a cartridge 1, a sample is moved, for example, to a first region 14 of the conduit 8 containing the hemocyte lysate, where it is solubilized, for example, by cycling between forward and reverse pump action. Following a predetermined incubation period, the sample-lysate mixture then is moved, for example, by pump action to a second region 16 of the conduit 8 containing the chromogenic substrate, where it is solubilized, for example, by cycling between forward and reverse pump action. The sample-lysate-substrate mixture then is moved to a third region containing a reaction inhibitor. Afterwards, the sample-lysate-substrate mixture then is moved to optical cell 6 for measurement of an optical property, for example, the absorbance or transmittance properties of the sample by an optical detector. The optical property of the sample-lysate-substrate mixture at a certain predetermined time point may then be interpolated onto a predetermined standard curve, for example, showing absorbance, optical density, or transmittance on the Y axis versus endotoxin concentration on the X axis, to give the concentration of the microbial contaminant in the sample.

4. Single-Step Kinetic Assay

A single-step kinetic assay, for example, a single step-chromogenic assay, is described in U.S. Pat. No. 5,310,657. Briefly, the kinetic chromogenic assay includes the steps of (i) simultaneously solubilizing a hemocyte lysate with a sample to be analyzed and a chromogenic substrate, (ii) incubating the resulting mixture at a temperature of about 0° to about 40° C., preferably about 25° to about 40° C., over a predetermined time range, and (iii) measuring a time required for a colorimetric change to reach a pre-selected value or a ratio in change of the colorimetric readout, using a conventional spectrophotometer.

Referring to FIG. 2A, in order to perform a kinetic chromogenic assay in a cartridge 1, a sample is moved, for.example, by pump action, to a first region 14 of the conduit 8 containing both the hemocyte lysate and chromogenic substrate, where it is solubilized, for example, by cycling between forward and reverse pump action. The sample-lysate-substrate mixture then is moved to optical cell 6 for measurement of an optical property for example, the absorbance or transmittance properties of the sample by an optical detector. The detector may determine how long it takes for each optical property to exhibit, for example, a 5% drop in optical transmittance. Results from multiple assays, for example, two assays can be averaged. The resulting values may then be interpolated onto a predetermined standard curve, for example, showing the time for a preselected change in absorbance or transmittance (as the case may be) on the Y axis versus endotoxin concentration on the X axis, to give the concentration of the contaminant in the sample.

Of the above methods, the endpoint chromogenic assay and the single-step kinetic chromogenic assays currently are considered the most rapid, sensitive, and economic assays for the detection of microbial contaminants, for example, endotoxin. However, both assays have their limitations. The endpoint chromogenic assay is rapid (about 15 minutes) but typically can only detect endotoxin concentrations in a range that is limited to about one log range (for example, about 1 EU/mL to about 0.1 EU/mL), with a sensitivity of about 0.1 EU/mL. Although the single-step kinetic chromogenic assay measures endotoxin concentrations in a wider range of about 5 logs (for example, about 5 to about 0.05 EU/mL) with a high sensitivity of about 0.05 EU/mL, this method can be quite slow to run (about 30 minutes). Furthermore, neither the endpoint chromogenic assay nor the single-step kinetic chromogenic assay are readily adaptable for in-field performance. The multi-step kinetic assay overcomes the limitations in the endpoint chromogenic assay and the kinetic chromogenic assay.

6. Multi-step Kinetic Assay

Figure 7:
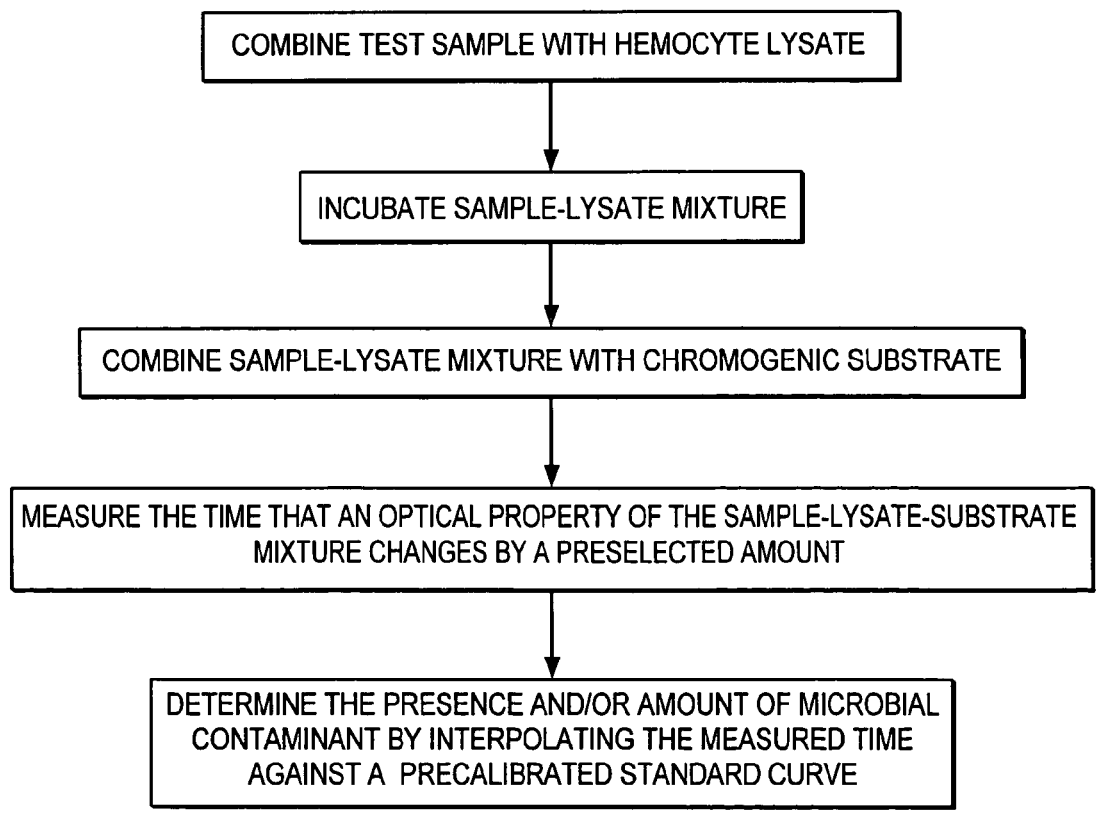
FIG. 7 is a flow chart for an exemplary multi-step kinetic chromogenic assay of the invention.

As will be discussed in more detail, the cartridge may also be used to perform a multi-step kinetic assay. The various steps involved in the multi-step kinetic assay are shown schematically in FIG. 7. The assay is initiated by combining the sample to be tested with a volume of a hemocyte lysate to produce a sample-lysate mixture. The mixture then is incubated for a predetermined period of time. The sample-lysate mixture then is contacted with a substrate, for example, a chromogenic substrate, to produce a sample-lysate-substrate mixture. Thereafter, the time in which a preselected change in an optical property (for example, a specific change in an absorbance value or a specific change in a transmission value) is measured. The presence and/or amount of microbial contaminant may be then determined by interpolating the measured time against a pre-calibrated standard curve, for example, a standard curve showing the time to make a preselected change in optical property (absorbance or transmittance) on the Y axis versus endotoxin concentration on the X axis.

The standard curve may be created, for example, by adding increasing amounts of an agent, for example, an endotoxin, glucan, or other microbial cell wall component, in a blank sample, for example, pyrogen-free water. The time for which a preselected change in an optical property, for example, a preselected increase in absorbance or a preselected decrease in transmittance, is determined for each concentration of the microbial cell wall component. The various time measurements to achieve a standard change in optical property then are plotted as a function of the microbial cell wall component concentration. In general, the concentration of endotoxin is inversely proportional to the time necessary to achieve the standard change in optical property. The standard curve can then be used to assess the presence and/or amount of microbial contaminant in the sample of interest. The calculation of standard curves is provided in Example 2.

As will be apparent to one skilled in the art, the relative amounts of hemocyte lysate and substrate can be adjusted to ensure that effective amounts of these two components are present in the sample-lysate-substrate mixture at the end of the assay. The final amount of hemocyte lysate protein in the assay is from about 1 µg to about 500 µg, preferably about 50 µg. The final amount of the substrate, for example, the chromogenic substrate in the assay is from about 1 µg to about 50 µg, preferably about 6.5 µg. The determination of the concentration and composition of the substrate, for example, the chromogenic substrate, is considered to be within the level of skill in the art.

The final volume of the resulting sample-lysate-substrate mixture can be based on the requirements of the optical detector used to measure the change in optical property of the sample. The ratio of volumes between the sample, lysate, and substrate can be readily established by those of ordinary skill in the art. Depending on the relative volumes of the sample, lysate, and substrate in the sample-lysate-substrate mixture, the concentration of the other components of the assay can be adjusted to maintain the final concentrations in the operable range, as described herein.

Referring to FIG. 2A, to perform the multi-step kinetic assay in a cartridge 1 of the invention, a sample is first moved, for example, by pump action, to a first region 14 containing the hemocyte lysate, where it is mixed and incubated for a predetermined period of time. The sample-lysate mixture then is moved, for example, by pump action, to the second region 16 containing the substrate, for example, the chromogenic substrate, where it is solubilized. The sample-lysate-substrate mixture then is moved to optical cell 6, for a measurement of an optical property. The time intervals required for mixing and incubating steps are pre-programmed for optimal sensitivity and microbial contaminant concentration range.

Figure 8A:
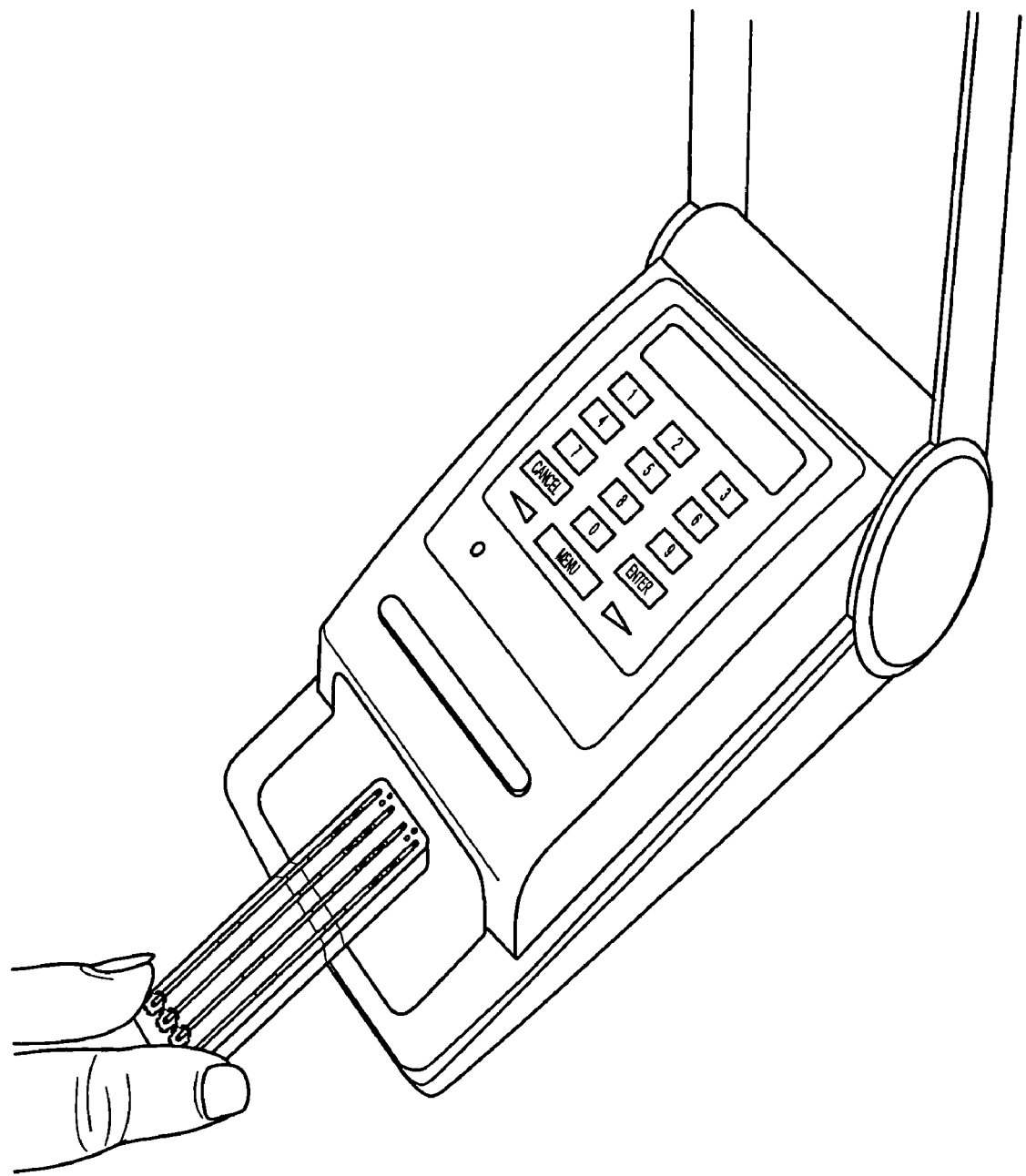
Figure 8B:
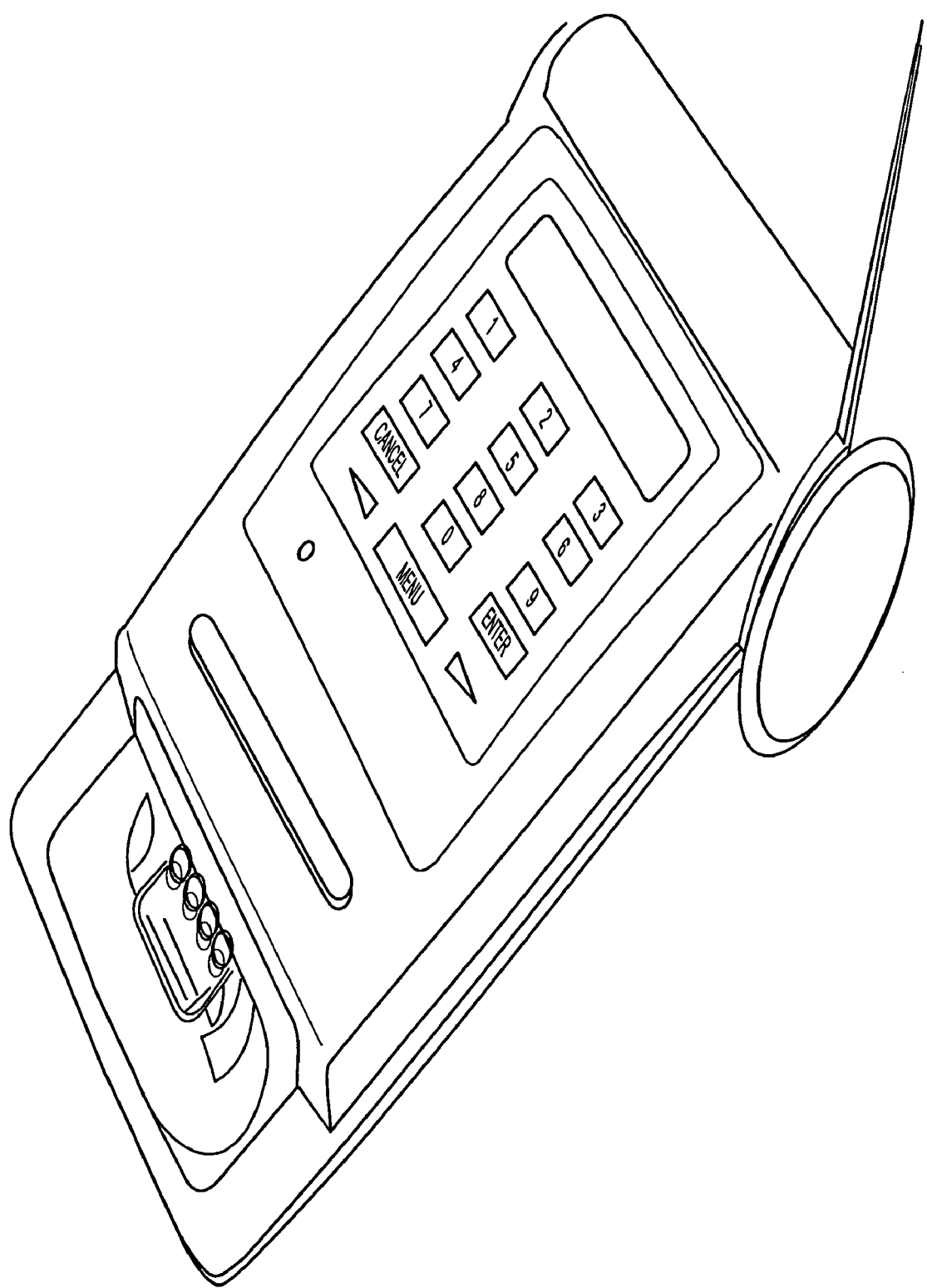

FIGS. 8A and 8B show an exemplary cartridge and hand held optical detector useful in the practice of the invention. FIG. 8A shows the cartridge being introduced into the detector and FIG. 8B shows the cartridge inserted into the detector with the fluid inlet ports still exposed to the user.

Figure 9:
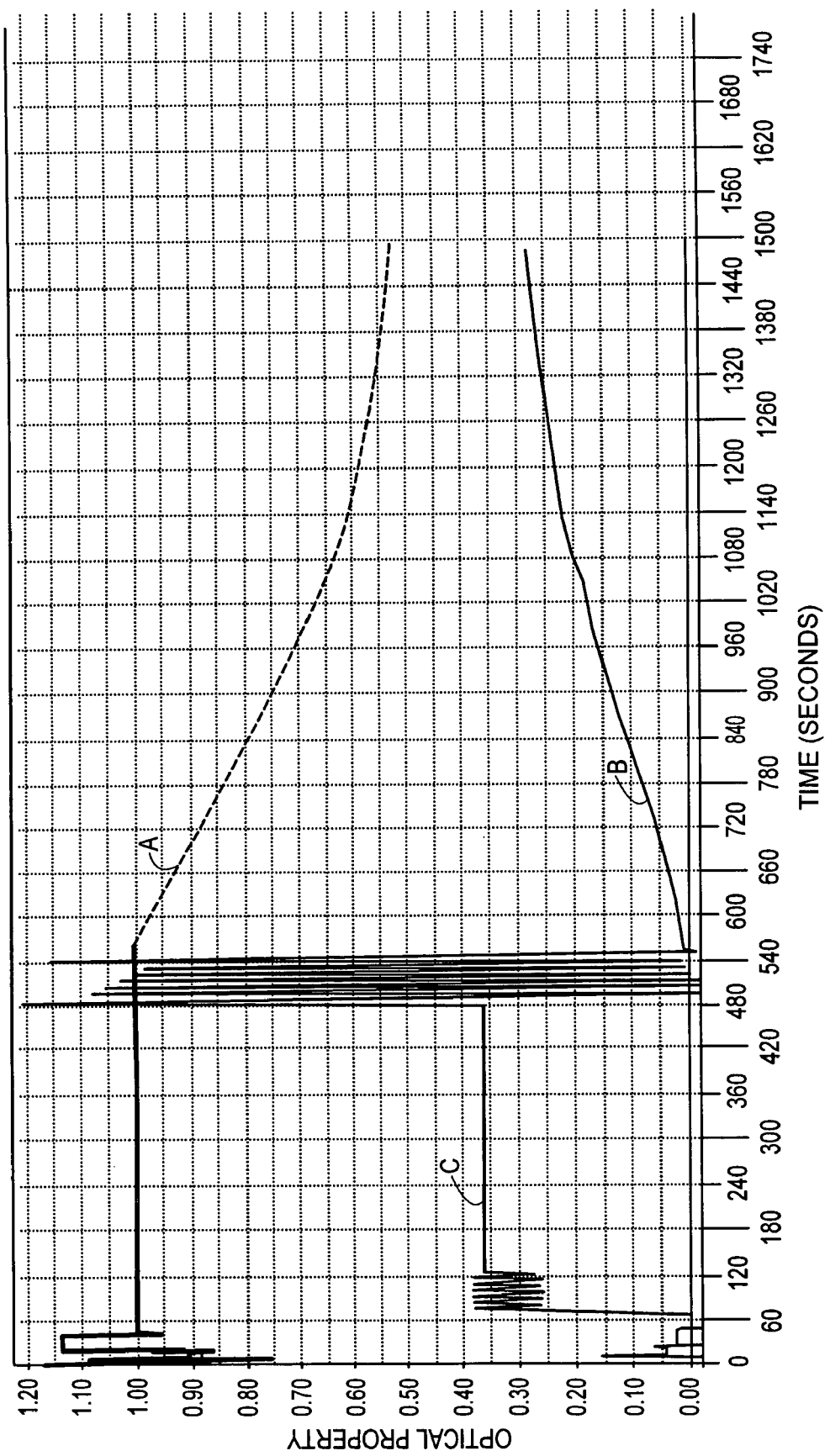
FIG. 9 is a graphical representation showing changes in light absorbance or optical density (full line) or light transmittance (dashed line) through an optical cell of an exemplary cartridge of the invention during a multi-step kinetic chromogenic assay.

FIG. 9 is a graph showing the changes in optical properties that can be generated in a cartridge using a multi-step kinetic assay. The dashed line represents changes in transmittance of the sample over time. The solid line represents changes in absorbance of the sample over time. Referring to FIGS. 2A and 9, optical properties were monitored after an aliquot of sample was added to the fluid inlet port 4 at a time of 0 seconds. After 60 seconds, the sample was drawn to region 14, where it was mixed with hemocyte lysate disposed on region 14 for 60 seconds (represented by vertical zig zag lines from T=60 to T=120). The amplitude of the mixing (length of the vertical lines) is determined such that the sample is repeatedly moved over the entire region 14. Thereafter, the sample-lysate mixture was incubated from 120 to 480 seconds at region 14 without further mixing. After 480 seconds, the sample was drawn to a chromogenic substrate at region 16 and the sample-lysate mixture combined with the chromogenic substrate from the period shown from 480 to 540 seconds (represented by vertical zig zag lines from T=480 to T=540). The amplitude of the mixing (length of the vertical lines) is determined such that the sample is repeatedly moved over the entire region 16. The resulting sample-lysate-substrate mixture then was drawn to optical cell 6 and the optical properties (absorbance and transmittance) measured for the period from 540 second to 1440 seconds.

Using the initial absorbance or transmittance readings of the mixture, the time required for the absorbance or transmittance to change by an arbitrary amount (Reaction Time) is determined. The amount of microbial contaminant in the sample then is determined by comparing the Reaction Time for the sample against a predetermined standard curve.

A spiked sample is assayed in parallel with the unspiked sample. The microbial contaminant concentration in the unspiked sample and the microbial contaminant recovered in the spiked sample can be compared to determine the presence of interference, such as an inhibitor or an enhancer of the reaction, as previously described.

Although the multi-step assay may be performed in a cartridge of the type discussed above, it may be employed in a variety of other formats, for example, within the well of a microtiter plate. Exemplary assays performed in the well of a microtiter plate are discussed in Example 3. Multiple samples of various test fluids, as well as spiked samples and the series of control samples making up a standard curve, may be placed in the wells of the microplate. Fixed amounts of hemocyte lysate and then substrate are added to each of the wells, preferably using an automated system, such as a robot, and the plate processed by a microplate reader, which can be programmed to sequentially read the absorbance of each well in a repetitive fashion.

In addition, it is contemplated that the cartridges, glucan-specific assays, and the multi-step kinetic assays can be used to detect the presence and/or amount of a ligand of interest in a test sample. For example, by adapting the assay format as appropriate, it is possible to detect the presence and/or amount of any ligand of interest, for example, a drug, toxin, protein, metabolite, in a sample. An exemplary ligand assay performed in the well of a microtiter plate is discussed in Example 7. By way of example, a binder for a ligand of interest, for example, an antibody or antigen binding fragment thereof, is immobilized on the surface of a solid support, for example, in a cartridge or a microplate. The binder is then pre-loaded or pre-bound with a complex comprising the ligand of interest coupled or bound to lipopolysaccharide or glucan. Methods for conjugating glucan or lipopolysaccharide to a ligand are well known in the art. For example, Boutonnier et al. (2001) INFECT. IMMUN. 69:3488-3493, describe methods for conjugating lipopolysaccharide to tetanus toxoid (see also, Konadu et al. (1994) INFECT. IMMUN. 62:5048-5054; Kenne et al. (1982) CARBOHYDR. RES. 100:341-349). When a sample containing the ligand of interest is combined with the immobilized binder, the lipopolysaccharide or glucan-labeled ligand is displaced. The amount of displaced ligand can then be quantified by the extent of the lipopolysaccharide or glucan initiated reaction of a LAL preparation.

Using these principles, it is possible to create a cartridge for determining the presence and/or amount of a ligand of interest in a sample. In this type of format, the binder for ligand is immobilized on a surface of the conduit downstream of the sample inlet port and upstream of the optical cell. The binder for ligand is then preloaded with a complex comprising the ligand of interest coupled or conjugated to, for example, lipopolysaccharide or glucan. A hemocyte lysate (for example, a Factor G-specific lysate for detecting displaced glucan, or a Factor C-specific lysate for detecting displaced lipopolysaccharide) is immobilized on a surface of the conduit downstream of the immobilized binder for ligand. When the sample of interest is applied to the sample inlet port, the sample passes the binder for ligand. To the extent that the sample contains the ligand, the ligand displaces the complex from the immobilized binder. The amount of displaced ligand can be measured by measuring a change in an optical property in the hemocyte lysate. This change in optical property can then be correlated with the amount of the ligand of interest in the sample.

EXAMPLES

Practice of the invention will be more fully understood from the following examples, which are presented herein for illustrative purposes only, and should not be construed as limiting the invention in any way.

Example 1

Preparation of the Chromogenic Assay Cartridge

An exemplary cartridge shown in FIGS. 2 was prepared as follows. Referring to FIG. 5A, the LAL and chromogenic substrates were applied to regions 14' and 16', respectively, of conduit 8' of the bottom half 2 of the cartridge 1 using a Hamilton Microlab 540B Dispenser (Hamilton Company, Reno, Nev.). Briefly, 4-5.0 µL of 10 mg/mL Endosafe LAL (Charles River Endosafe, Charleston, S.C.) containing 1% mannitol (Osmitrol, Baxter, Deerfield, Ill.) and 0.1% dextran (MW 10-100K, Sigma-Aldrich, St. Louis, Mo.), was applied to regions 14'. 4-5.0 µL of (1.3 mg/mL) chromogenic substrate Ile-Glu-Ala-Arg-pNA Chromogenix S-2423 (Instrumentation Laboratories, Milan, Italy) containing 1% polyvinyl alcohol (PVA) (MW 7K-30K, Sigma-Aldrich, St. Louis, Mo.), was applied to regions 16'. The bottom half 2 of the cartridge 1 was dried under a controlled temperature of 25° C. +/−2° C. and a humidity of 5% +/−5% in a Lunaire Environmental Steady State & Stability Test Chamber (Lunaire Environmental, Williamsport, Pa.) in a Puregas HF200 Heatless Dryer (MTI Puregas, Denver, Colo.) for 1 hour. Temperature and humidity was controlled by a Watlow Series 96 1/16 DIN Temperature Controller (Watlow Electric Manufacturing Company, St. Louis, Mo.).

Referring to FIG. 5B, 5 µl Endosafe CSE endotoxin (Charles River Endosafe, Charleston, S.C.) ("spike") was applied to region 14" of the conduit 8" of the top half 3 of the cartridge 1. The top half 3 of the cartridge 1 was dried under a controlled temperature of 25° C. +/−2° C. and a humidity of 5% +/−5% for one hour, as described above.

Following fabrication, the two halves 2 and 3 were assembled such that regions 14' and 14" were aligned one on top of the other, and the edges of the cartridge halves 2 and 3 ultrasonically sealed using a Dukane Model 210 Ultrasonic Sealer (Dukane Corporation, St. Charles, Ill.) under the control of a Dukane Dynamic Process Controller (Dukane Corporation, St. Charles, Ill.).

The resulting cartridge 1 was labeled to identify the lot number of the cartridge, in order to later identify the standard curves used to quantify the microbial contaminant in the sample. The sealed, labeled cartridge 1 then was placed into a laminated foil pouch along with a desiccant such as silica gel or molecular sieve. The foil pouch was purged with nitrogen gas and then sealed with a PAC Model PV-G Vacuum Impulse Heat Sealer (Packaging Aids Corporation, San Rafael, Calif.).

Example 2

Cartridge-based Assays

This example demonstrates that a cartridge of the invention can be used to measure the amount of a microbial contaminant by an endpoint chromogenic assay, kinetic chromogenic assay and a multi-step chromogenic assay.

FIG. 8 shows how the cartridge of the invention may be used with a portable hand-held optical detector. FIG. 8A shows the cartridge in the process of being inserted into the optical detector. FIG. 8B shows the cartridge inserted fully into the optical detector, however, the fluid inlet ports of the cartridge are still accessible to the user. This configuration permits the user to apply one or more samples of interest to the exposed fluid inlet ports even though the optical cells of the cartridge are located in place within the optical detector.

(I) Endpoint Chromogenic Assay in a Cartridge

Figure 10A:
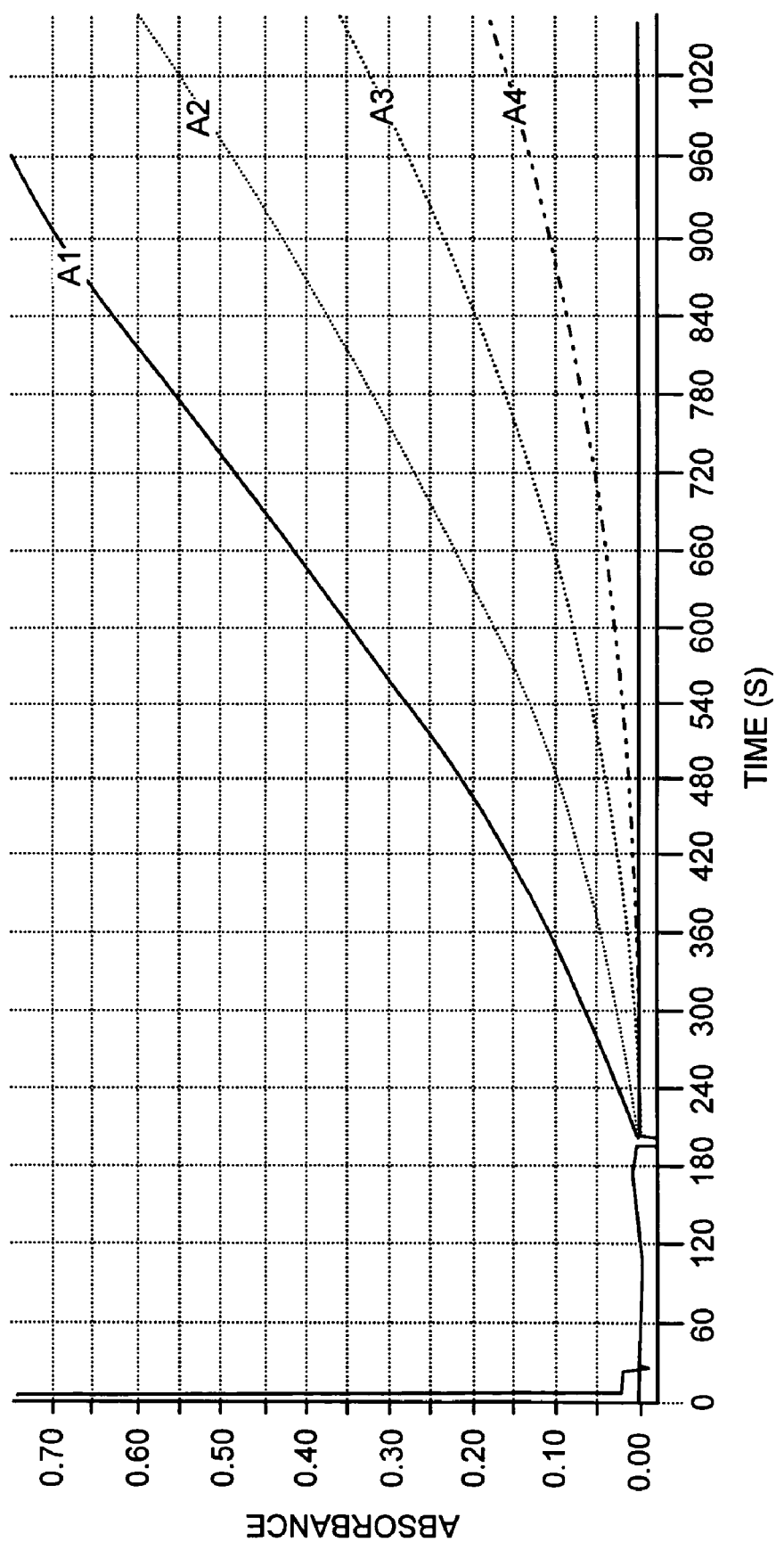
FIGS. 10A-10B are graphical representations of absorbance values in an end point chromogenic assay where
Figure 10B:
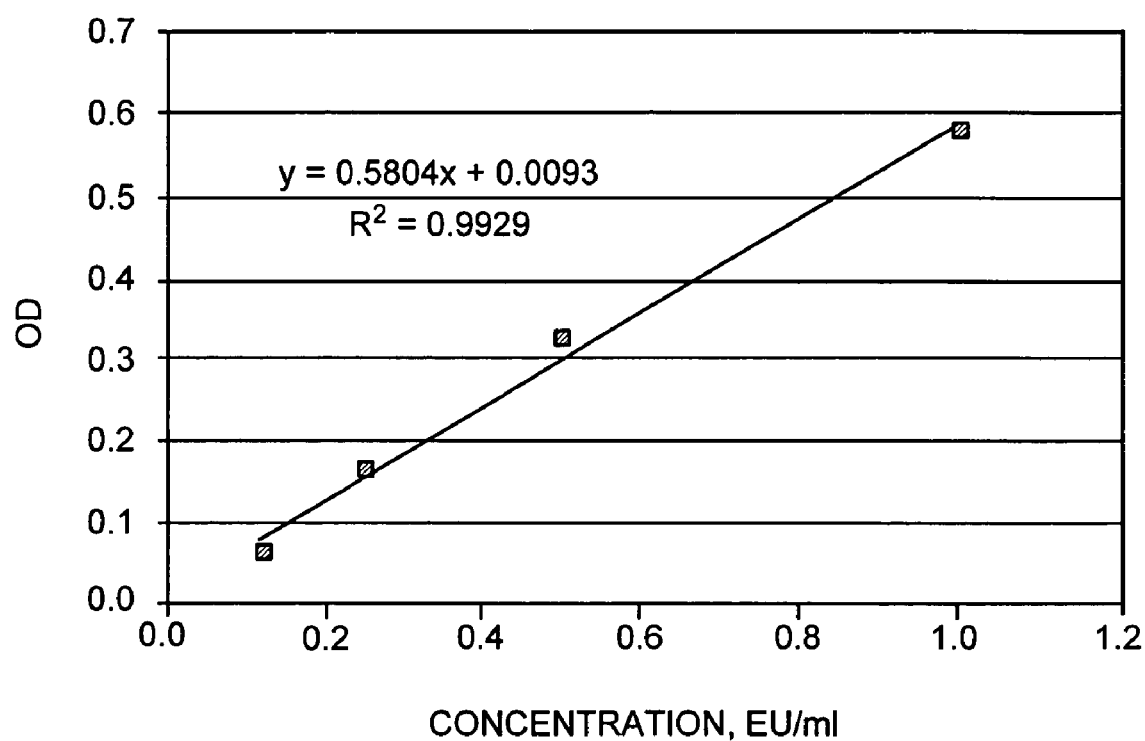

A cartridge was prepared essentially as described in Example 1, with the exception that no spikes were added to the conduits. Samples of endotoxin standards of 1.0 EU/mL, 0.5 EU/mL, 0.25 EU/mL, and 0.125 EU/mL were prepared and 25 µL of each were pipetted into one of four cartridge fluid inlet ports. The portable optical detector maintained a temperature of 37° C. for the duration of the test. The portable optical detector was programmed to perform a series of steps. The portable optical detector first drew each endotoxin sample into the region of a conduit that contained dried LAL, and mixed and incubate the sample with the LAL for 120 seconds (T=60 to T=180). The portable optical detector then drew the endotoxin sample-LAL mixture to the region in the conduit containing dried chromogenic substrate, and mixed the sample-LAL mixture with the substrate for 5 seconds. The portable optical detector then drew the sample-LAL-substrate mixture to the optical cell. The portable optical detector then recorded absorbance data from each of the four channels. After about 10 minutes (about 780 seconds), the test was ended by reading the last absorbance (optical density) value. The absorbance value curves for each endotoxin sample are shown in FIG. 10A. The absorbance values generated at 780 seconds were recorded and plotted as a function of endotoxin concentration (FIG. 10B) to give a standard curve. This standard curve can be used to determine the concentration of endotoxin in a sample of interest, when the sample is treated in the same manner as the standards.

(II) Single-Step Kinetic Chromogenic Assay in a Cartridge

A cartridge was prepared essentially as described in Example 1, with the exceptions that the chromogenic substrate was applied to the same region as the LAL and that no spikes were added to the conduits. Samples of endotoxin standards of 5.0 EU/mL, 0.5 EU/mL, and 0.05 EU/mL were prepared, and 25 μL of the 5 EU/mL standard was pipetted into two fluid inlet ports of the cartridge. The portable optical detector maintained a temperature of 37° C. for the duration of the test. The portable optical detector was programmed to perform a series of steps. The portable optical detector first drew each endotoxin sample into the region of a conduit that contained both dried LAL and chromogenic substrate, and mixed and incubated the sample with the LAL and substrate for 30 seconds. The portable optical detector then drew the sample-LAL-substrate mixture to the optical cell. The portable optical detector began recording absorbance for both samples. The assay was repeated for the 0.5 EU/mL and 0.05 EU/mL standards.

Figure 11A:
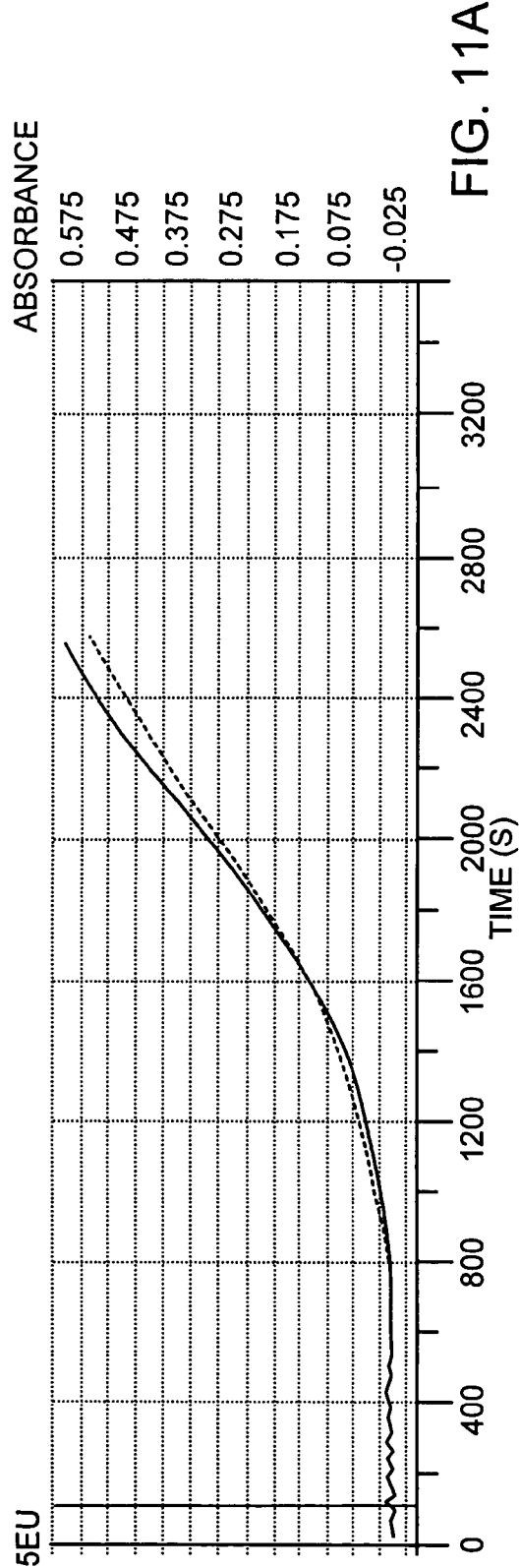
FIGS. 11A-11D are graphical representations of absorbance values for a kinetic chromogenic assay performed in a cartridge of the invention, where
Figure 11B:
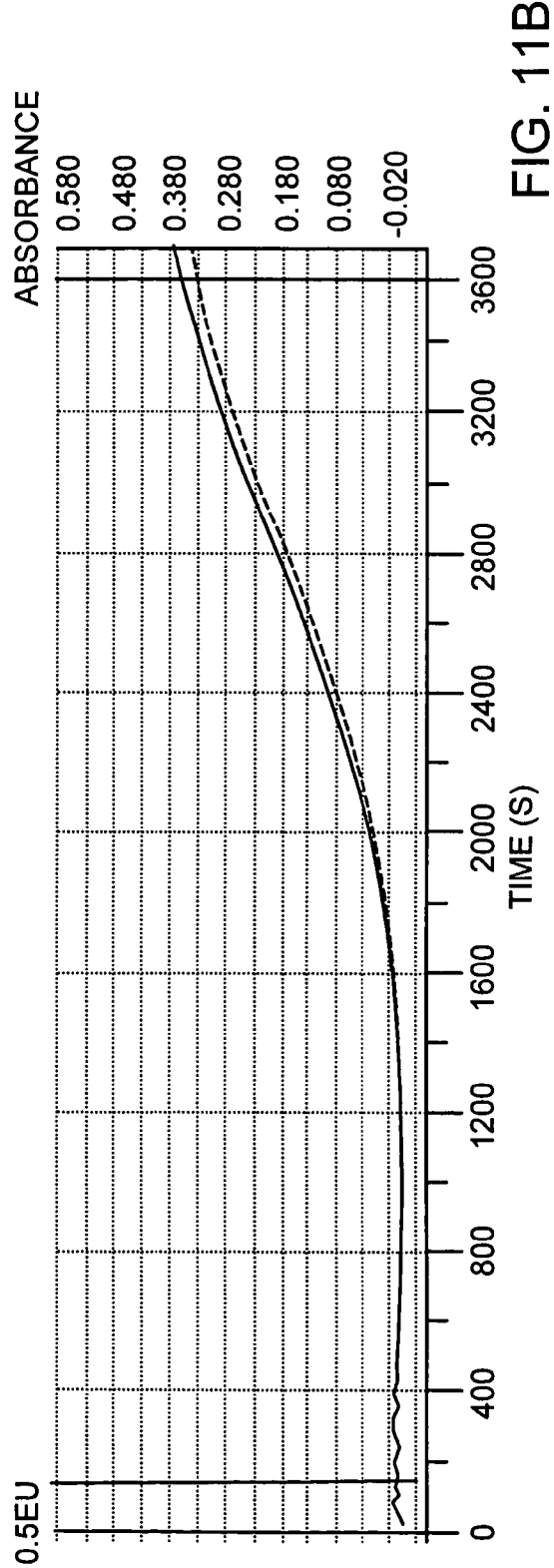
Figure 11C:
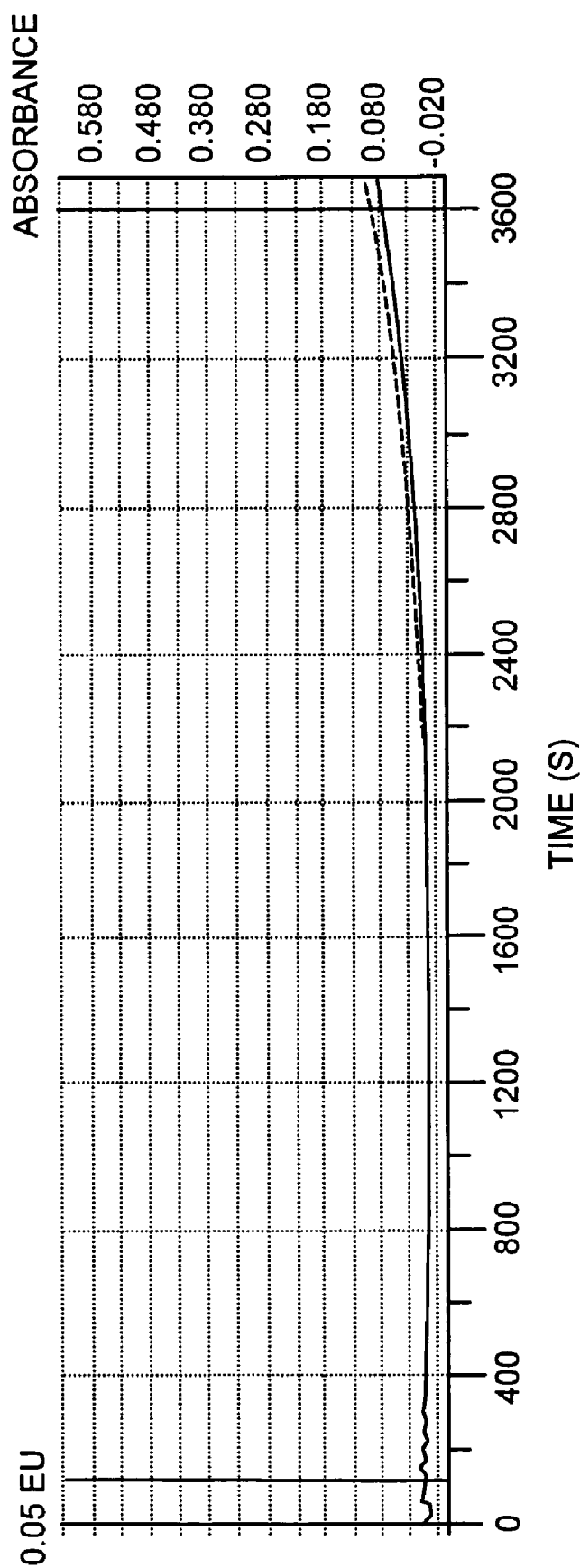
Figure 11D:
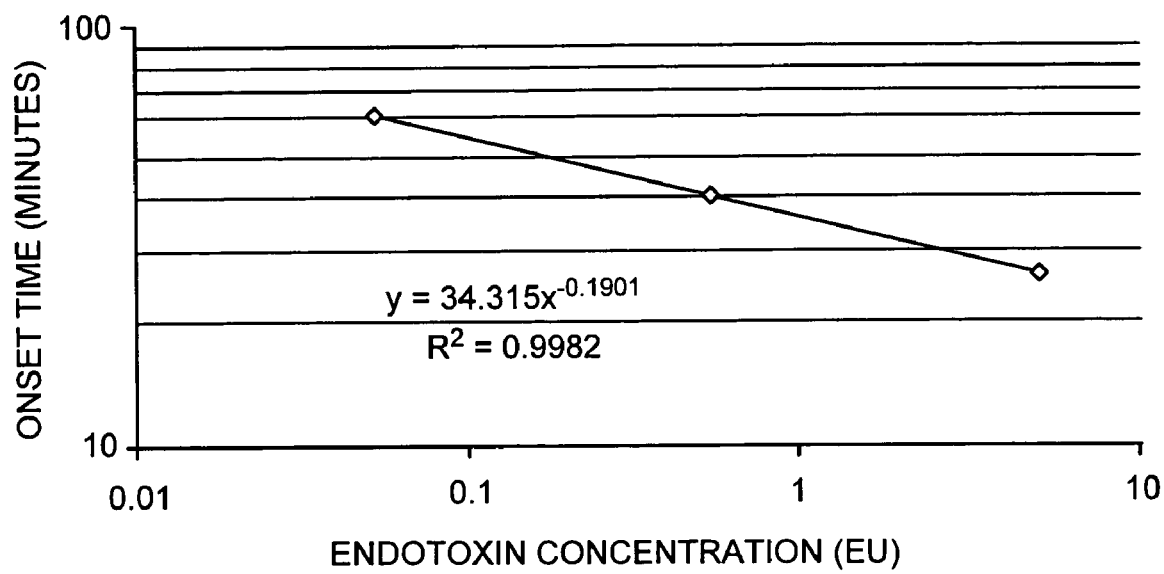

The plots of recorded data for each endotoxin standard are shown in FIGS. 11A, 11B, and 11C. The time taken for the optical density of each endotoxin standard-LAL-substrate mixture to reach an optical density of 0.05 was recorded as the onset time for each standard. A plot of the log of the endotoxin concentration (X axis) vs. the log of the onset times (Y axis) provides a kinetic standard curve (FIG. 11D). This standard curve can be used to determine the concentration of endotoxin in a sample of interest when the sample is treated in the same manner as the standards.

(III) Multi-step Kinetic Assay in a Cartridge

Figure 12:
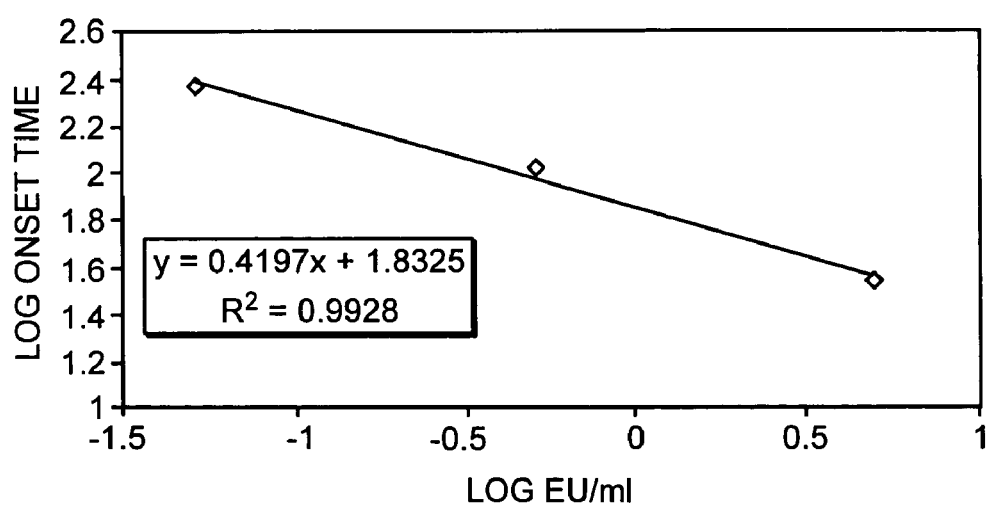
FIG. 12 is a graphical representation of a standard curve for a multi-step kinetic chromogenic assay performed in a cartridge of the invention, generated by plotting the log of endotoxin concentration (X-axis) versus the log of absorbance value at onset time (Y axis)

A cartridge was prepared essentially as described in Example 1, with the exception that no spikes were added to the conduits. Samples of endotoxin standards of 1.0 EU/mL, 0.5 EU/mL, 0.25 EU/mL, and 0.125 EU/mL were prepared and 25 μL of each were pipetted into one of four cartridge fluid inlet ports. The portable optical detector maintained a temperature of 37° C. for the duration of the test. The portable detector was programmed to perform a series of steps. The portable optical detector first drew each endotoxin sample into the region of a conduit that contained dried LAL, and mixed and incubate the sample with the LAL for 240 seconds. The portable optical detector then drew the endotoxin sample-LAL mixture to the region in the conduit containing dried chromogenic substrate and mixed the sample-LAL mixture with the substrate for 20 seconds. The portable optical detector then drew the sample-LAL-substrate mixture to the optical cell. The portable optical detector began recording absorbance data from each of the four channels. The time taken for the optical density of each endotoxin standard-LAL-substrate mixture to reach an optical density of 0.05 was recorded as the onset time for each standard (see, Table 1). A plot of the log of the endotoxin concentrations (X axis) versus the log of the onset times (Y axis) provides a kinetic standard curve (FIG. 12). This standard curve can be used to determine the concentration of endotoxin in a sample when the sample is treated in the same manner as the standards.

TABLE 1

| | Endotoxin Concentration, EU/mL | | | |
|---|---|---|---|---|
| | 5.0 | 0.5 | 0.05 | 0 |
| Onset Time or Reaction Time (seconds) | 30 | 166 | 222 | 300 |

Example 3

Microplate-based Assays

This example demonstrates that a multi-well microtiter plate can be fabricated so that the amount of a microbial contaminant (bacterial endotoxin in this example) can be measured by an endpoint chromogenic assay, a single-step kinetic assay and a multi-step assay.

(I) Single-step Kinetic Assay on a Microplate

Figure 13:
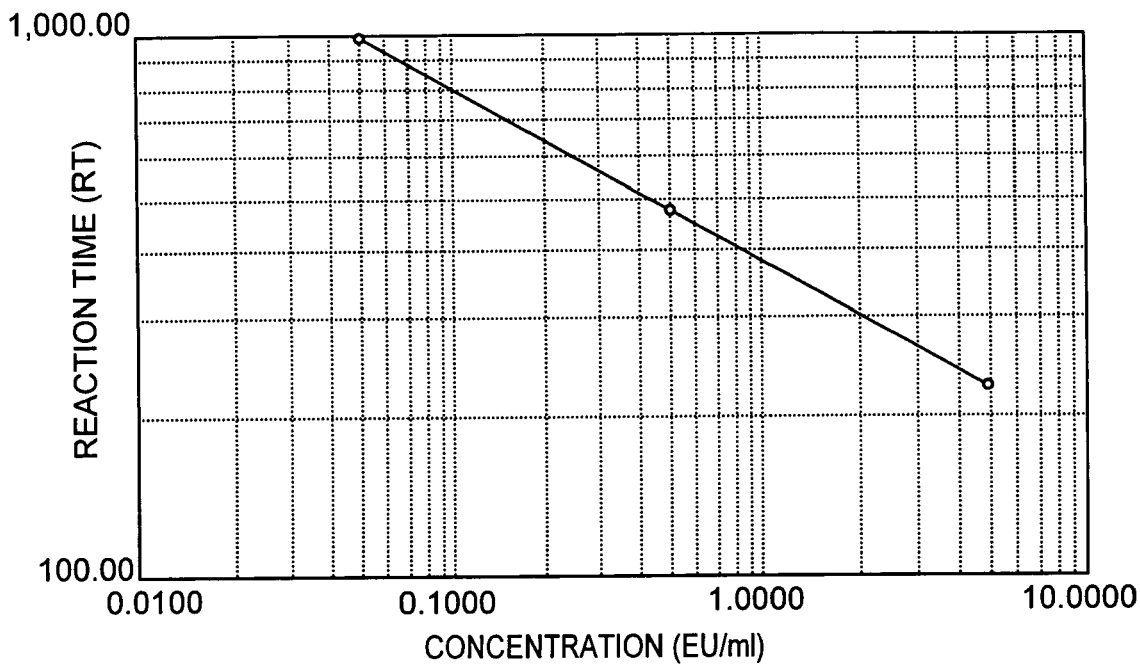
FIG. 13 is a graphical representation of a standard curve for a single-step kinetic chromogenic assay performed in a microtiter plate, generated by plotting the log of endotoxin concentration (X-axis) versus the log of absorbance value at onset time (Y axis)

A single-step kinetic chromogenic assay was performed as follows. Briefly, 50 μL of a control microbial contaminant of interest (e.g., 5 EU/mL, 0.5 EU/mL, or 0.05 EU/mL of Endosafe Control Standard Endotoxin (CSE), Charles River Endosafe, Charleston, S.C.), was added to one or more wells of a 96 well plate. 50 μL of 5 mg/mL Endosafe LAL (Charles River Endosafe, Charleston, S.C.) and 5 μL of 1.3 mg/mL Chromogenix S-2423 chromogenic substrate (Instrumentation Laboratories, Milan, Italy) were added to each well and incubated at 37° C. for 32 minutes. The optical density of the mixture in each well was monitored by a spectrophotometer, such as a Sunrise micro plate reader (Tecan, Research Triangle Park, N.C.). The time taken for each standard to change 0.1 absorbance units was determined ("onset time"). The results are summarized below in Table 2. A plot of the log of the endotoxin concentrations (X axis) versus the log of the onset times (Y axis) provides a kinetic standard curve (FIG. 13). This standard curve may be used to measure the concentration of endotoxin in a sample of interest, when the sample is treated in the same manner as the standards.

TABLE 2

| Standard | Concentration, EU/mL | Time to Onset OD/ Max Reaction Time (seconds) | Mean Time to Reach Onset OD (seconds) | Standard Deviation | (RT) CV % | Calculated Value |
|---|---|---|---|---|---|---|
| STD1 | 5.0 | 229.4/221.4 | 225.4 | 4.0/4.0 | 1.77 | >4.9853 |
| STD2 | 0.5 | 472.2/465.0 | 468.6 | 3.59/3.59 | 0.77 | 0.5029 |
| STD3 | 0.05 | 982.5/977.1 | 979.8 | 2.68/2.68 | 0.27 | <0.0499 |
| CTRL1 | 0 | >990.0/>990.0 | >990.0 | 0.00/0.00 | 0.00 | <0.0500 |

(II) Endpoint Assay on a Microplate

Figure 14:
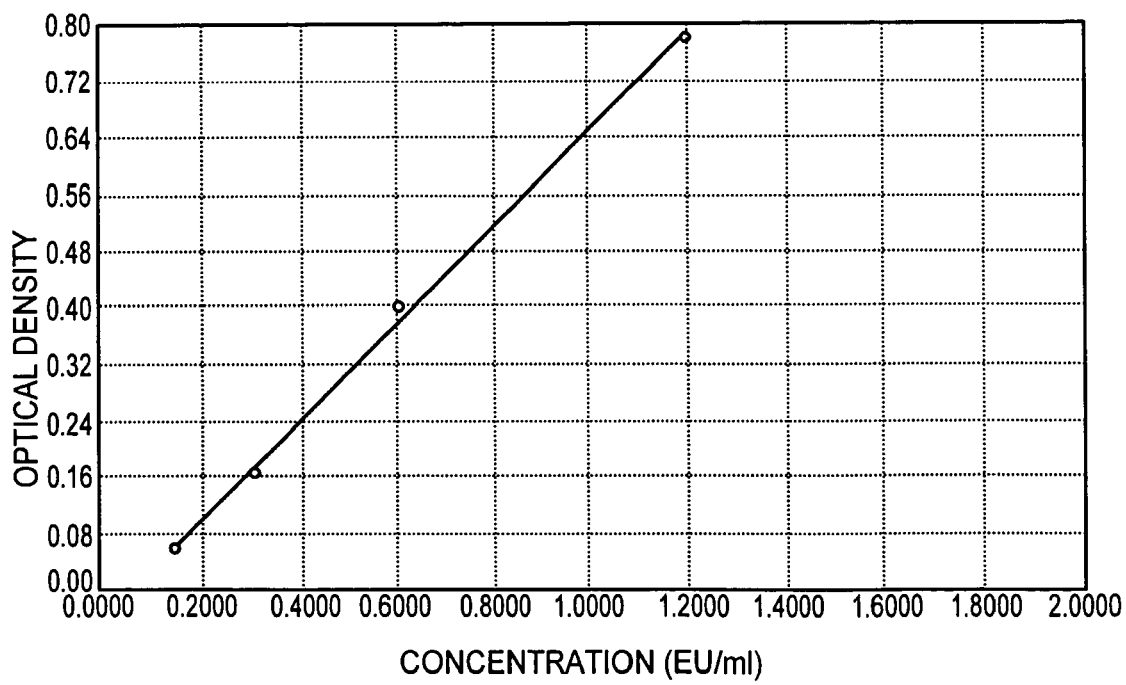
FIGS. 14 is a graphical representation of a standard curve for an endpoint chromogenic assay performed in a microtiter plate, generated by plotting the absorbance values (Y axis) of each concentration of endotoxin (X axis)

An endpoint chromogenic assay using the reagents in Example 3(I) was performed as follows. Briefly, 50 μL of a control microbial contaminant of interest (e.g., endotoxin) at a concentration of e.g., 5 EU/mL, 0.5 EU/mL, or 0.05 EU/mL, was added to one or more wells of a 96-well plate. 50)L of hemocyte lysate (5 mg/mL) was added to one or more wells containing the standard and incubated at 37° C. for 5 minutes. 5 μL of chromogenic substrate (1.3 mg/mL) was added to one or more wells and incubated at 37° C. for 5 minutes. The reaction then was stopped by the addition of 100 μL of 50% acetic aid to each well. The optical density of the mixture in each well was measured at 405 nm by a spectrophotometer, such as a Sunrise micro plate reader (Tecan, Research Triangle Park, N.C.). The absorbance of each sample at 780 seconds (shown in Table 3) was recorded. The absorbance of each sample (Y axis) was plotted versus the endotoxin concentration (X axis) to provide a standard curve (shown in FIG. 14). This standard curve may be used to measure the concentration of endotoxin in a sample of interest, when the sample is treated in the same manner as the standards.

Example 4

Preparation and Testing of Glucan-Specific LAL

As shown in FIG. 1, crude LAL reacts with both endotoxin (lipopolysaccharide) and glucan, so that cell wall material from both Gram negative bacteria and yeast/mold cells activate the coagulation cascade. In the case of Gram negative bacteria, coagulation is mediated through the Factor C cascade. In the case of yeast and mold, coagulation is mediated through the Factor G cascade. In order to determine which of the two contaminants is present in a sample, or what proportion of each might comprise a mixed contamination, LAL was produced under conditions to render it specific for glucan, as described below.

Amebocyte blood was mixed 6:1 with 0.05% Tween 20 (Sigma, St. Louis, Mo.), 150 mM NaCl and centrifuged in a Sorval model RC-3B centrifuge at 3,000 rpm for 5 minutes. The pelleted cells were washed with 0.01% Tween 20, 150 mM NaCl and centrifuged at 3,000 rpm for 5 minutes. The pelleted, washed cells were divided into three

TABLE 3

| Standard | Concentration, EU/mL | Optical Density (OD) | Mean Optical Density | Standard Deviation | (OD) CV % | Calculated Value |
| --- | --- | --- | --- | --- | --- | --- |
| STD1 | 1.2 | 0.7505/0.8105 | 0.7805 | 0.03/0.03 | 3.84 | 1.1876 |
| STD2 | 0.6 | 0.4135/0.3825 | 0.3980 | 0.02/0.02 | 3.89 | 0.6319 |
| STD3 | 0.3 | 0.1655/0.1615 | 0.1635 | 0.00/0.00 | 1.22 | 0.2912 |
| STD4 | 0.15 | 0.0655/0.0525 | 0.0590 | 0.01/0.01 | 11.02 | 0.1393 |
| CTRL1 | 0 | 0.0115/−0.0115 | 0.0000 | 0.01/0.01 | 0.00 | <0.1500 |

(III) Multi-step Kinetic Assay on a Microplate

Figure 15:
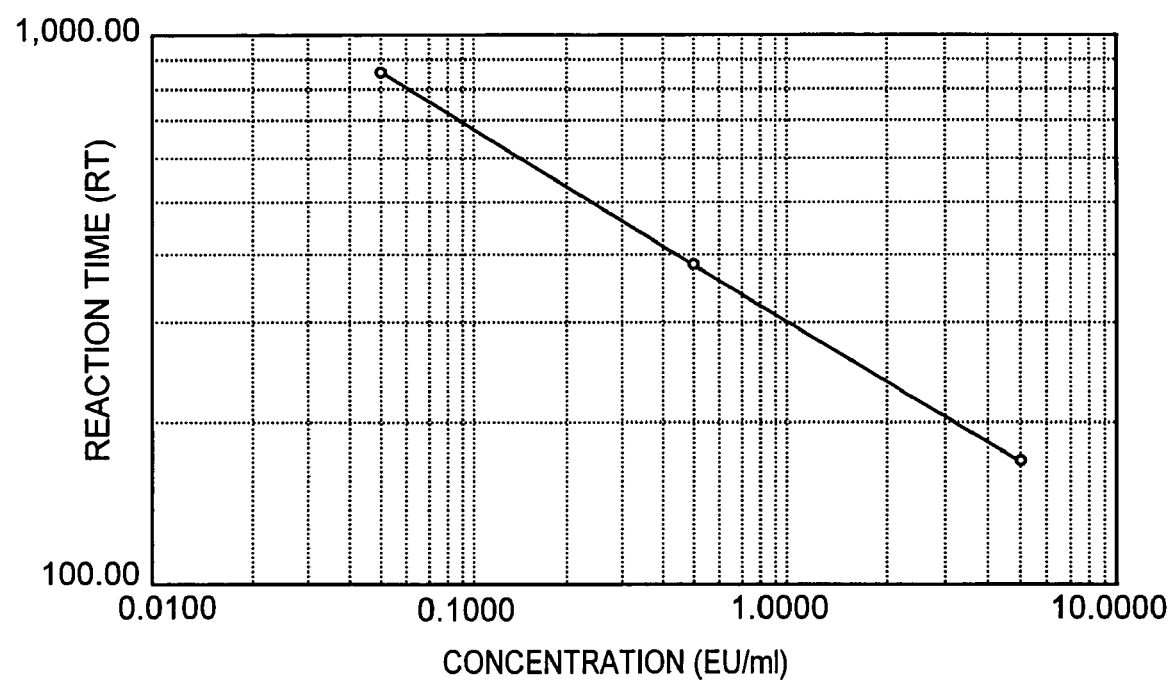
FIG. 15 is a graphical representation of a standard curve for a multi-step kinetic chromogenic assay performed in a microtiter plate, generated by plotting the log of endotoxin concentration (X-axis) versus the log of absorbance value at onset time (Y axis).

A multi-step kinetic chromogenic assay using the same reagents as in Example 3(I) was performed as follows. Briefly, 50 μL of a control microbial contaminant of interest, for example, endotoxin, at the following concentrations of 5 EU/mL, 0.5 EU/mL, or 0.05 EU/mL, was added to one or more wells of a 96-well plate. 50 μL of hemocyte lysate (5 mg/mL) was added one or more wells and incubated at 37° C. for 3 minutes. 5 μL of chromogenic substrate (1.3 mg/mL) was added to one or more wells containing the standard and incubated at 37° C. for 16.5 minutes. The optical density of the mixture in each well was monitored by a spectrophotometer, such as a Sunrise micro plate reader (Tecan, Research Triangle Park, N.C.). The time taken for each microbial contaminant standard and/or sample to change 0.1 absorbance units was determined ("onset time"). The results are summarized in Table 4. A plot of the log of the endotoxin concentrations (X axis) versus the log of the onset times (Y axis) provides a kinetic standard curve (FIG. 15). This standard curve may be used to measure the concentration of endotoxin in a sample of interest, when the sample is treated in the same manner as the standards.

aliquots, resuspended in either lipopolysaccharide-free water, lipopolysaccharide-free 1 M NaCl, or lipopolysaccharide-free 2 M NaCl. The cells in each pellet were lysed by sonication for 1-2 minutes. Cell debris was removed by centrifugation at 4,000 rpm for 10 minutes, and the resulting supernatant was harvested and used directly in coagulation experiments.

Figure 16A:
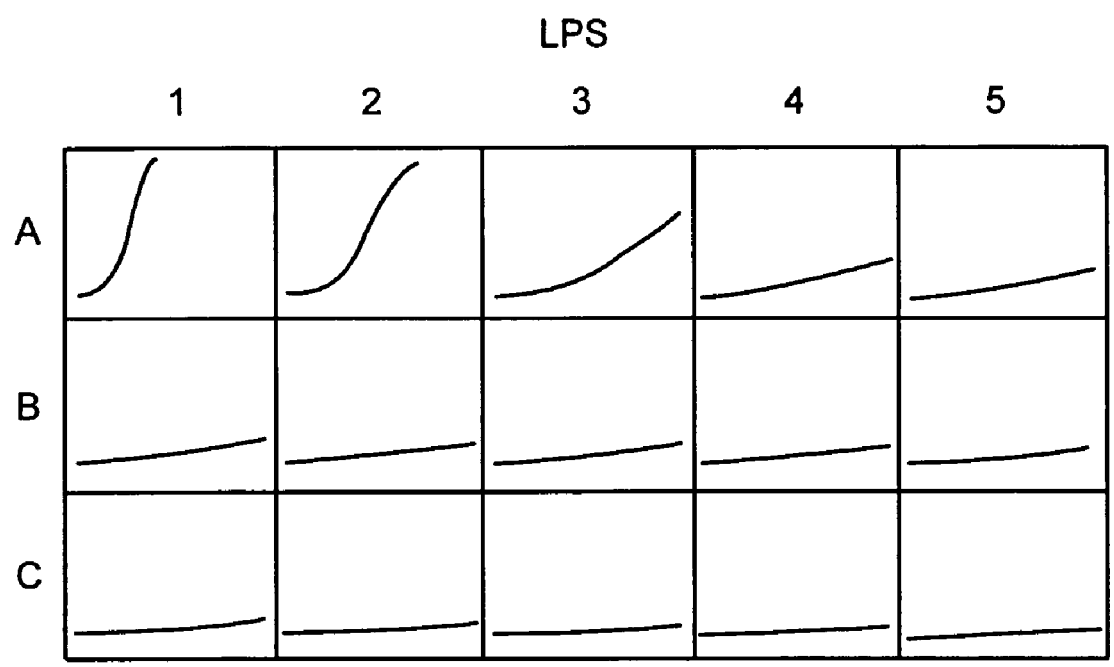
FIGS. 16A-B are graphical representations of amebocyte lysate kinetic reactions for standard LAL and glucan-specific LAL.
Figure 16B:
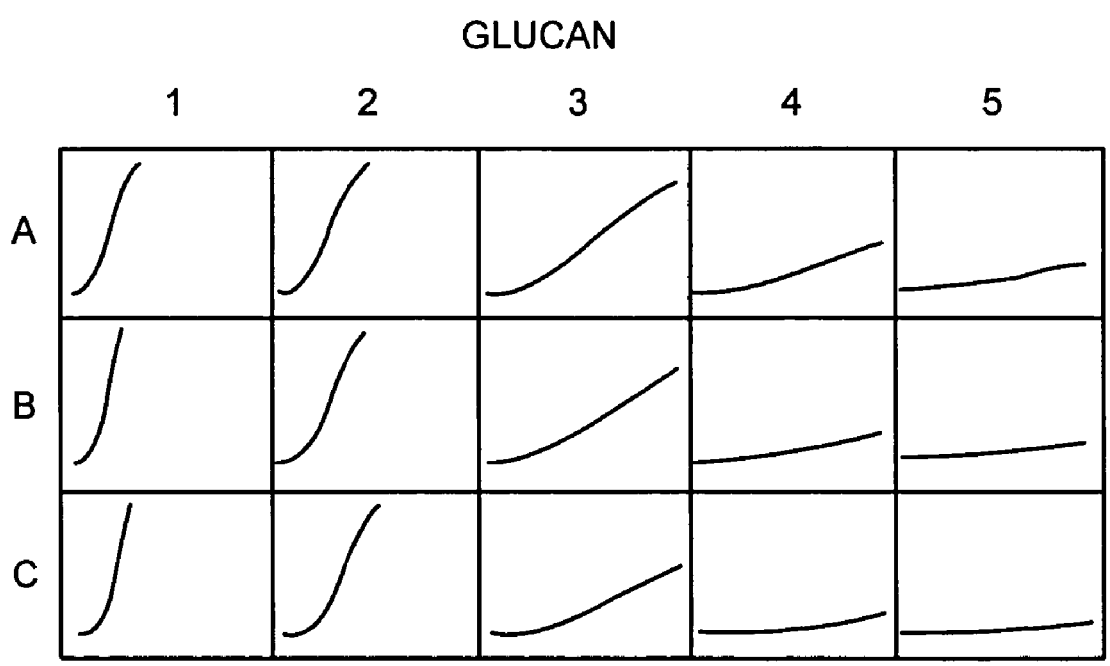

FIG. 16 provides a graphical representation of kinetic coagulation reactions using various concentrations of lipopolysaccharide (FIG. 16A) or glucan (FIG. 16B) in a microtiter plate multi-step kinetic assay, such as that described in Example 3 (III) with either standard LAL (row A of each figure) or glucan-specific LAL (rows B and C in each figure).

FIG. 16A illustrates the reactivity of the lysates with lipopolysaccharide (Charles River Endosafe) serially diluted 1:10 from column 1 to column 5. The lipopolysaccharide concentrations in columns 1 through 5 are: 10 ng/ml, 1 ng/ml, 100 pg/ml, 10 pg/ml, and 0, respectively.

FIG. 16B illustrates the reactivity of the lysates with glucan (Charles River Endosafe, Charleston, S.C.) serially diluted 1:10 from column 1 to column 5. Glucan concen-

TABLE 4

| Standard | Concentration, EU/mL | Time to Onset OD/ Max Reaction Time (seconds) | Mean Time to Reach Onset OD (seconds) | Standard Deviation | (RT) CV % | Calculated Value |
| --- | --- | --- | --- | --- | --- | --- |
| STD1 | 5.0 | 172.1/166.4 | 169.3 | 2.84/2.84 | 1.68 | >5.1505 |
| STD2 | 0.5 | 393.8/387.7 | 390.7 | 3.03/3.03 | 0.78 | 0.4712 |
| STD3 | 0.05 | 851.7/843.3 | 847.5 | 4.17/4.17 | 0.49 | <0.0515 |
| CTRL1 | 0 | >990.0/>990.0 | >990.0 | 0.00/0.00 | 0.00 | <0.0500 | trations from column 1 through 5 are: 100 µg/ml, 10 µg/ml, 1 µg/ml, 100 ng/ml, and 0, respectively.

In each figure, row A shows the reactivity with standard LAL prepared from cells lysed in pyrogen-free water (i.e., reactive with both glucan and lipopolysaccharide). In each figure, row B is glucan-specific LAL produced by lysing cells in 1 M NaCl. In each figure, row C is glucan-specific LAL produced by lysing cells in 2M NaCl. Each graph represents the change in optical density or absorbance, as shown on the Y axis, over time, as shown on the X axis. For example, in FIG. 16A, the graph shown in row A, column 1, shows the change in absorption over time when 10 ng/ml lipopolysaccharide is added to standard LAL.

The results demonstrate that when lipopolysaccharide is added to standard lysate, the lipopolysaccharide activates the lysate to produce an increase in absorbance (see, FIG. 16A, row A). However, the rate of absorbance change decreases as less lipopolysaccharide is added to each sample. The results demonstrate, however, that there is substantially no change in absorbance as lipopolysaccharide is added to each glucan-specific lysate (see, FIG. 16A, rows A and B).

The results also demonstrate that when glucan is added to standard lysate, the glucan (like the lipopolysaccharide) activates the lysate to produce an increase in absorbance (see, FIG. 16B, row A). However, the rate of absorbance change decreases as less glucan is added to each sample. In contrast to the situation when lipopolysaccharide was added, the glucan activates each glucan-specific lysate to produce an increase in absorbance over time (see, FIG. 16B, rows B and C).

These results demonstrate that it is possible to produce a glucan-specific lysate using the protocol described herein.

Example 5

Testing of Glucan-Specific LAL in a Cartridge-based Multi-Step Assay

Glucan-specific LAL was prepared by lysing amebocytes in 2M NaCl as described in Example 4 and tested in a cartridge-based multi-step kinetic assay, such as that described in Example 2(111).

Figure 17:
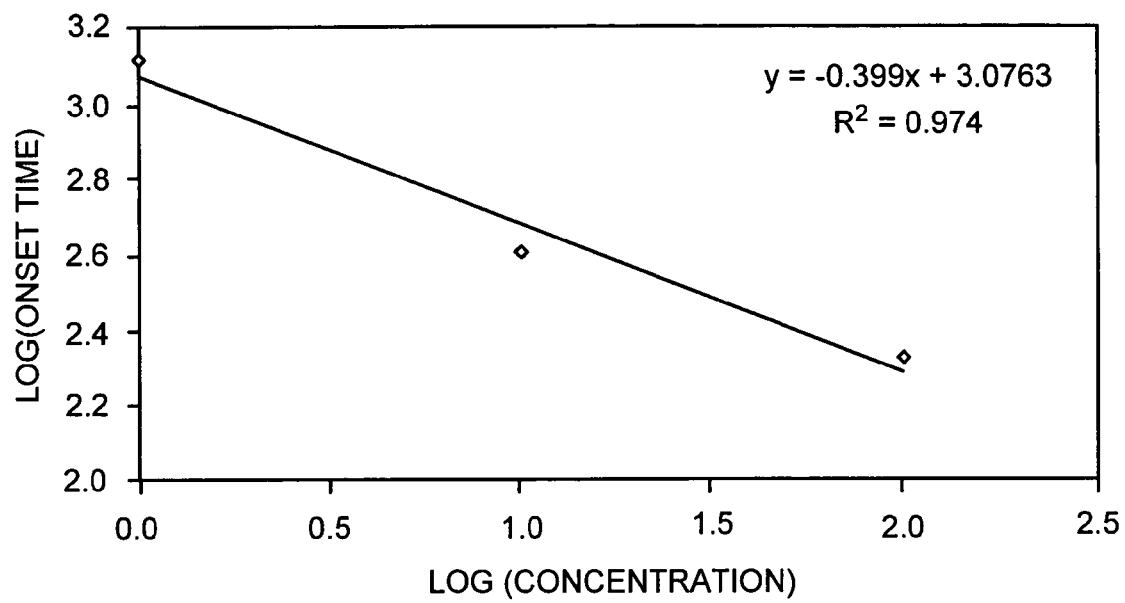
FIG. 17 is a graphical representation of a logarithmic plot of a glucan standard curve obtained using a multi-step kinetic assay.

Samples containing glucan at 100 µg/ml, 10 µg/ml, 1 µg/ml, 100 ng/ml, and 0, were incubated with the glucan-specific lysate for 4 minutes. The resulting mixture was mixed with a chromogenic substrate, acetate-Ile-Glu-Ala-Arg-pNA and the change in absorbance at 405 nm was measured over time. The time required to reach an onset optical density of 0.05 was collected (see, Table 5) and the log of the glucan concentration was plotted versus the log of the time to reach onset O.D. (see, FIG. 17).

TABLE 5

| Glucan Standard (µg/ml) | Onset Time (seconds) | Calculated µg/ml glucan activity |
|---|---|---|
| 100 | 207 | 80.5 |
| 10 | 400 | 15.4 |
| 1 | 1300 | 0.80 |
| 0.1 | >1800 | <0.36 |
| Negative control | >1800 | <0.36 |

The data show that it is possible to produce a standard curve of glucan concentration using a cartridge-based multi-step assay. The standard curve can then be used to determine the concentration of glucan in a sample of interest, when the sample is treated in the same manner as the standards.

Example 6

Means of Reading an LAL Reaction Using Fluorescent Substrates

A cartridge-based multi-step kinetic LAL assay, such as that described in Example 2(III), was performed using the fluorogenic substrate: Glu-Gly-Arg-AMC (Enzyme Systems Products, Livermore, Calif.). The cartridge was modified to include a long-pass filter placed between the sample and the light sensor such that light having the excitation wavelength (390 nm) was blocked but yet the emissions at a wavelength of 460+/−25 nm were able to pass through and be detected by the sensor.

Figure 18:
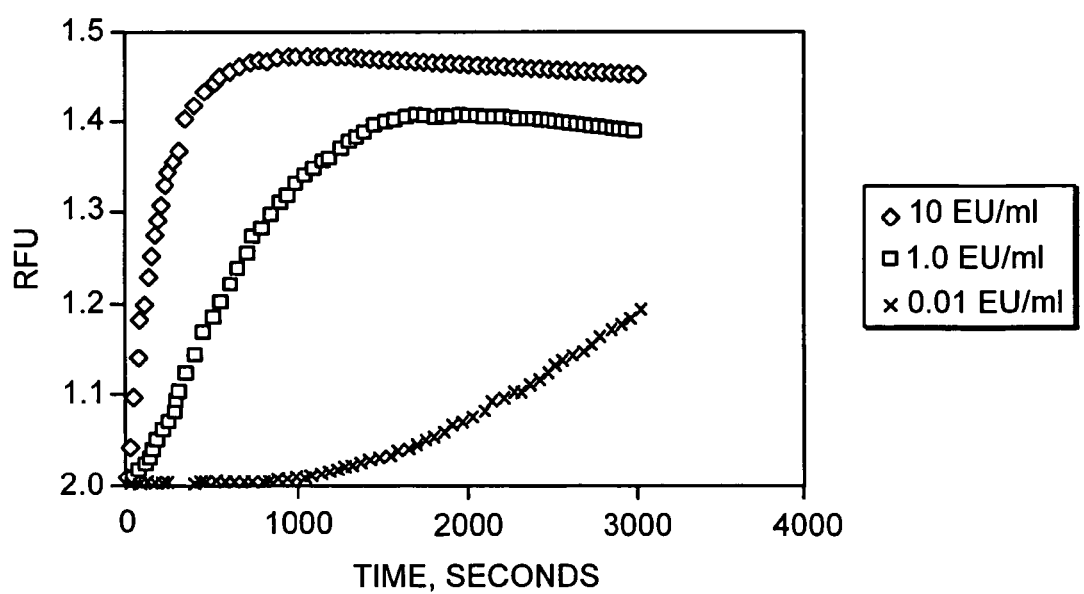
FIG. 18 is a graphical representation of an assay measuring the fluorescence emitted from different concentrations of a fluorogenic substrate Glu-Gly-Arg-AMC in a multi-step kinetic assay in the cartridge format.

Using the device, fluorescence data (expressed as Relative Fluorescence Units) were collected from samples containing 10 EU (Endotoxin units), 1 EU, and 0.1 EU. The changes in Relative Fluorescence Units over time are presented in FIG. 18. The results demonstrate that the multi-step kinetic assays can measure the amount of endotoxin in sample using a fluorescent substrate.

Example 7

Measurement of Lipopolysaccharide-labeled Ligand Using an Immobilized Antibody

The microtiter plate multi-step kinetic LAL assay, such as that described in Example 3(111) can also be used to measure the concentration of a ligand. Briefly, an antibody that binds a ligand of interest is immobilized onto the surface of a well of a microtiter plate. Then, the ligand binding sites of the antibody are preloaded with a complex comprising the ligand coupled to lipopolysaccharide. When a sample containing the ligand is exposed to the immobilized antibody, the lipopolysaccharide-labeled ligand is displaced and quantified by reaction with LAL. In this example, the ligand detected was fluorescein. An anti-fluorescein antibody was immobilized onto the surface of a well and was pre-loaded with fluorescein-labeled lipopolysaccharide. When samples containing fluorescein-labeled antibody were exposed to the immobilized antibody, the fluorescein-lipopolysaccharide conjugate was released from the immobilized antibody and measured by reactivity with LAL.

Briefly, rabbit anti-fluorescein antibody (Virostat, Portland Me.) was diluted 1/4000 in CAPS buffer, pH 10.2 (Sigma, St. Louis, Mo.). 25 µl of the diluted antibody was added to the wells of a high binding plate (Coming 25801) and incubated for 1 hour at 37° C. The plate was washed 4×100 µl per well with TTBS (0.1% Tween, 100 mM Tris buffered saline) using a multipipettor. The wells were blocked by adding 150 µl per well of gelatin diluent and stored at 4° C. overnight. The wells then were washed with 3×100 µl per well with TTBS. Lipopolysaccharide (LPS)-fluorescein (FITC) conjugate (List Biological Laboratory, Campbell, Calif.) was diluted from 1 µg/ml to 10 pg/ml using 10-fold dilutions in 0.1 M Tris. 0.1 M Tris was used as a control. 75 µl of diluted LPS/FITC conjugate was added per well and incubated for 30 minutes at 37° C. The wells then were washed with 3×100 µl per well with 0.1 M Tris.

Fluorescein-labeled goat anti-chicken antibody (Southern Biotech. Associates Inc 6100-02, Birmingham, Ala.) was diluted 1/50, 1/150, and 1/450 in 0.1 M Tris. 0.1 M Tris was used as a control. 75 µl of fluorescein-labeled goat anti-chicken antibody was added per well and incubated for 30 minutes at 37° C. 50 µl was removed from each well and transferred to a clean 96-well plate (Falcon, 353072, Becton Dickenson, Franklin Lakes, N.J.). 50 µl Endochrome K (Charles River Endosafe), which is a 1:1 mixture of LAL substrate and LAL lysate, was added to each well. The plate was read at time intervals (e.g., kinetically) at 405 nm at 37° C. for 60-90 minutes (Min OD: 0, Max OD: 0.8, Onset OD: 0.1).

Figure 19:
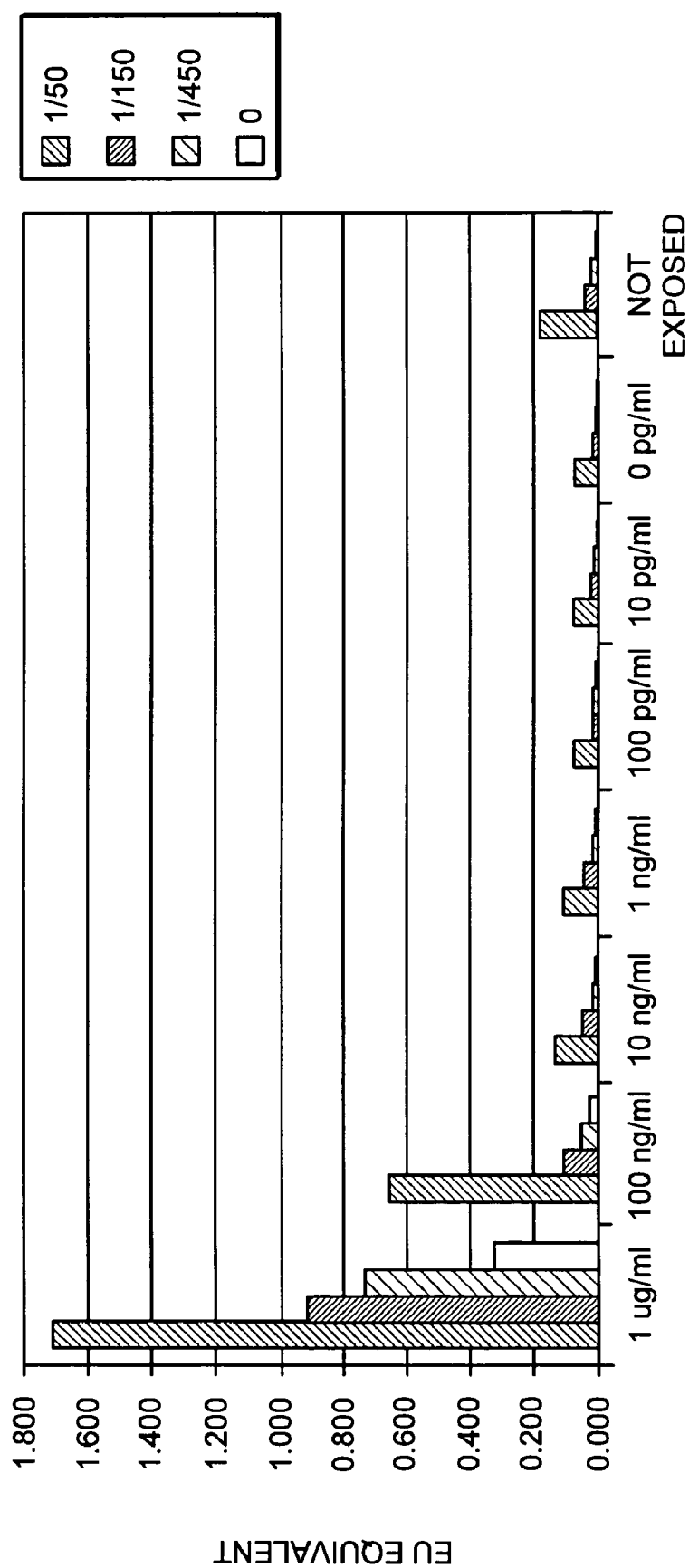
FIG. 19 is a graphical representation showing the proportional displacement of various concentrations of lipopolysaccharide-fluorescein isothiocyanate (1 µg/ml, 100 ng/ml, 10 ng/ml, 1 ng/ml, 100 pg/ml, 10 pg/ml, and control) by different dilutions of a fluorescein-labeled ligand (1/50, 1/150, and 1/450).

To find the proper concentration of LPS/FITC to be pre-bound to the immobilized antibody, increasing concentrations were applied to the plate from 10 pg/mL to 1 µg/mL. Then dilutions of the fluorescein-labeled antibody ligand were exposed to the immobilized antibody and the displaced LPS/FITC measured as EU equivalents. As shown in FIG. 19, at the 1 µg/mL level of LPS/FITC, an EU proportional to the ligand was achieved (far left). Accordingly, by using this type of format, it is possible to detect the presence and/or measure the amount of a ligand of interest in a test sample.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

INCORPORATION BY REFERENCE

All publications and patent documents cited in this application are incorporated by reference in their entirety for all purposes to the same extent as if the entire contents of each individual publication or patent document was incorporated herein.

What is claimed is:

1. A cartridge for determining the presence or amount of a microbial contaminant in a sample, the cartridge comprising:
   (i) a housing defining a fluid inlet port, an optical cell, and a conduit having a fluid contacting surface for providing fluid flow communication between the fluid inlet port and the optical cell; and
   (ii) a hemocyte lysate and an anti-flaking agent dried on a region of the fluid contacting surface of the conduit, wherein, when a sample is applied to the fluid inlet port, the sample traverses the region and solubilizes the hemocyte lysate during transport to the optical cell.

2. The cartridge of claim 1, further comprising a chromogenic substrate disposed on a second, different region of the fluid contacting surface.

3. A cartridge for determining the presence or amount of a microbial contaminant in a sample, the cartridge comprising:
   (i) a housing defining a fluid inlet port, an optical cell located downstream of the fluid inlet port, a first conduit having a fluid contacting surface for providing fluid flow communication between the fluid inlet port and the optical cell, a pump port located downstream of the optical cell, and a conduit connecting the optical cell and the pump port;
   (ii) a hemocyte lysate dried on a first region of the fluid contacting surface of the first conduit; and
   (iii) a chromogenic substrate dried on a second, different region of the fluid contacting surface of the first conduit,
   wherein, when a sample is applied to the fluid inlet port, the sample traverses the first and second regions and solubilizes the hemocyte lysate and chromogenic substrate during transport to the optical cell.

4. The cartridge of claim 2 or 3, wherein the second region is located downstream of the first region.

5. The cartridge of claim 1 or 3, further comprising a preselected amount of an agent representative of the microbial contaminant disposed on the fluid contacting surface of the conduit.

6. The cartridge of claim 5, wherein the agent is disposed on the first region.

7. The cartridge of claim 5, wherein the agent is a bacterial endotoxin or a $(1 \rightarrow 3)$-$\beta$-D glucan.

8. A cartridge for determining the presence or amount of a microbial contaminant in a sample, the cartridge comprising:
   (i) a housing defining
   a first fluid inlet port, a first optical cell, and a first conduit having a fluid contacting surface for providing fluid flow communication between the first fluid inlet port and the first optical cell, and
   a second fluid inlet port, a second optical cell, and a second conduit having a fluid contacting surface for providing fluid flow communication between the second fluid inlet port and the second optical cell;
   (ii) a first hemocyte lysate dried on a first region of the fluid contacting surface of the first conduit, so that when a sample is applied to the first fluid inlet port, the sample traverses the region and solubilizes the first hemocyte lysate during transport to the first optical cell;
   (iii) a second hemocyte lysate dried on a first region of the fluid contacting surface of the second conduit, so that when sample is applied to the second fluid inlet port, the sample traverses the region and solubilizes the second hemocyte lysate during transport to the second optical cell, and
   (iv) an agent representative of a microbial contaminant dried on the fluid contacting surface of the first conduit.

9. The cartridge of claim 8, further comprising a chromogenic substrate disposed on a second, different region of the fluid contacting surface of the first conduit.

10. The cartridge of claim 9, wherein the second region is located downstream of the first region.

11. The cartridge of claim 9, further comprising a chromogenic substrate disposed on a second, different region of the fluid contacting surface of the second conduit.

12. The cartridge of claim 11, wherein the second region is located downstream of the first region.

13. The cartridge of claim 8, wherein the agent is disposed on the first region.

14. The cartridge of claim 8, wherein the agent is a bacterial endotoxin or a $(1 \rightarrow 3)$-$\beta$-D glucan.

15. A method of detecting the presence of a microbial contaminant in a sample, the method comprising the steps of:
   (a) introducing a sample into the sample inlet port of the cartridge of claim 1, 8 or 3;
   (b) permitting the sample to move to the optical cell; and (c) measuring an optical property of the sample in the optical cell, wherein a change in the optical property is indicative of the presence of a microbial contaminant in the sample.

16. The method of claim 15, wherein the change in optical property is an increase in absorbance of light of a preselected wavelength.

17. The method of claim 15, wherein the change in optical property is a decrease in transmission of light of a preselected wavelength.

18. A method of determining the amount of a microbial contaminant in a sample, the method comprising the steps of:
   (a) introducing a sample into the sample inlet port of the cartridge of claim 1, 8 or 3;
   (b) permitting the sample to move to the optical cell;
   (c) measuring the time in which a preselected change occurs in an optical property of the sample in the optical cell; and
   (d) comparing the time measuring in step (c) against a predetermined standard curve to determine the amount of the microbial contaminant in the sample.

19. The method of claim 18, wherein the change in optical property is an increase in absorbance of light of a preselected wavelength.

20. The method of claim 18, wherein the change in optical property is a decrease in transmission of light of a preselected wavelength.

* * * * *